(12) United States Patent
Clapper et al.

(10) Patent No.: US 9,101,603 B2
(45) Date of Patent: Aug. 11, 2015

(54) TARGETING OF CYP1B1 IN THE TREATMENT OF HEAD AND NECK CANCER AND LUNG CANCER

(75) Inventors: Margie L. Clapper, Harleysville, PA (US); Ekaterina G. Shatalova, Philadelphia, PA (US); Sibele Meireles, Minas Gerais (BR)

(73) Assignee: Institute for Cancer Research, Philadelphia, PA (US)

( * ) Notice: Subject to any disclaimer, the term of this patent is extended or adjusted under 35 U.S.C. 154(b) by 0 days.

(21) Appl. No.: 13/990,650

(22) PCT Filed: Nov. 30, 2011

(86) PCT No.: PCT/US2011/062639
§ 371 (c)(1),
(2), (4) Date: May 30, 2013

(87) PCT Pub. No.: WO2012/075136
PCT Pub. Date: Jun. 7, 2012

(65) Prior Publication Data
US 2013/0251732 A1  Sep. 26, 2013

Related U.S. Application Data

(60) Provisional application No. 61/418,075, filed on Nov. 30, 2010.

(51) Int. Cl.
| | |
|---|---|
| A61K 31/353 | (2006.01) |
| A61K 31/05 | (2006.01) |
| C07K 16/40 | (2006.01) |
| C12N 15/113 | (2010.01) |
| A61K 39/395 | (2006.01) |

(52) U.S. Cl.
CPC .............. *A61K 31/353* (2013.01); *A61K 31/05* (2013.01); *A61K 39/3955* (2013.01); *C07K 16/40* (2013.01); *C12N 15/1137* (2013.01); *C12Y 114/14001* (2013.01); *C12N 2799/027* (2013.01)

(58) Field of Classification Search
CPC .............................. A61K 31/353; A61K 31/05
See application file for complete search history.

(56) References Cited

U.S. PATENT DOCUMENTS

| | | |
|---|---|---|
| 6,797,471 B2 | 9/2004 | Katz et al. |
| 2003/0162727 A1 | 8/2003 | Murray et al. |
| 2010/0168180 A1 | 7/2010 | Potter et al. |

FOREIGN PATENT DOCUMENTS

| | | |
|---|---|---|
| WO | 0056773 | 9/2000 |
| WO | 0157444 | 8/2001 |

OTHER PUBLICATIONS

Saini et al., Functional significance of cytochrome P450 1B1 in endometrial carcinogenesis. Cancer Res. 69, 7038-45, 2009.*
Gribben, J. G., et al., "Unexpected Association between Induction of Immunity to the Universal Tumor Antigen CYP1B1 and Response to Next Therapy", Clin. Cancer Res., 2005; 11:4430-4436.
Chunsheng, L., et al., "Therapeutic MicroMRNA Strategies in Human Cancer", The AAPS Journal, vol. 11, No. 4, Dec. 2009, pp. 747-757.
Tsuchiya, Y., et al., "MicroRNA Regulates the Expression of Human Cytochrome P450 1B1", Cancer Res., 2006, 66:9090-9098.
Gentleman, R.C., et al., "Bioconductor: open software development for computational biology and bioinformatics", Genome Biology, 2004, vol. 5, Issue 10, pp. R80.1-R80.16.
Ritchie, M.E., et al., "A comparison of background correction methods for two-colour miccroarrays", Bioinformatics, vol. 23, No. 20, 2007, pp. 2700-2707.
Smyth, G.K., et al., "Linear models and empirical bayes methods for assessing differential expression in microarray experiments", Stat. Appl. Genet. Mol. Biol., 2004; 3, pp. 1-28.
Doostdar, H., et al., "Bioflavinoids: selective substrates and inhibitors for cytochrome P450 CYP1A and CYP1B1", Toxicology, 144 (2000), pp. 31-38.
International Search Report dated Jul. 6, 2012 in counterpart application PCT/US11/62639.
Port, et al., "Tobacco smoke induces CYP1B1 in the aerodigestive tract", Carcinogenesis (2004), vol. 25, pp. 2275-2281.
Kassis, et al., "Tumor invasion as dysregulated cell motility", Cancer Biology, vol. 11, 2001, pp. 105-117.
McFadyen, et al., "Cytochrome P450 enzymes: Novel options for cancer therapeutics", Molecular Cancer Therapeutics, 2004, vol. 3, No. 3, pp. 363-371.
Barnes, I., et al., World Health Organization Classification of Tumours. Pathology and Genetics of Head and Neck Tumours. IARC Press: Lyon 2005, pp. 140-143 and 177-181.
Travis, E.D., et al., World Health Organization Classification of Tumours. Pathology and Genetics of Tumours of the Lung, Pleura, Thymus and Heart. IARC Press: Lyon 2004, pp. 68-72.

* cited by examiner

*Primary Examiner* — Ruixiang Li
(74) *Attorney, Agent, or Firm* — Stradley Ronon Stevens & Young, LLP

(57) ABSTRACT

Methods for inhibiting the motility or proliferation of premalignant and malignant cells are provided. Methods for treating a malignancy of the head and neck and for treating a malignancy of the lung are also provided.

17 Claims, 10 Drawing Sheets

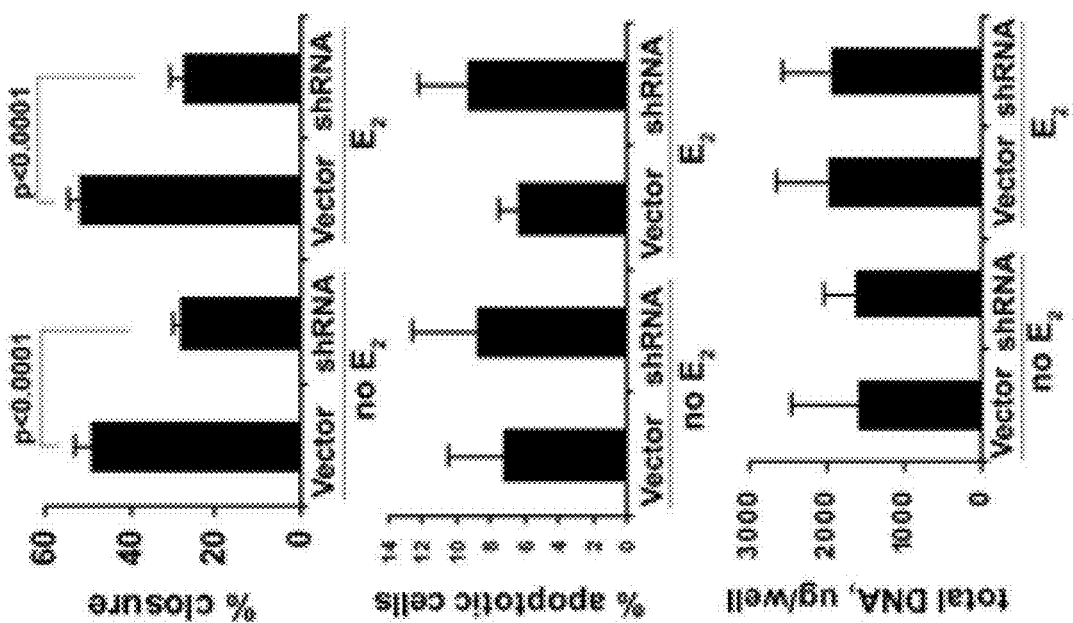
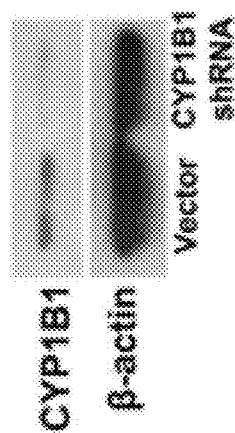
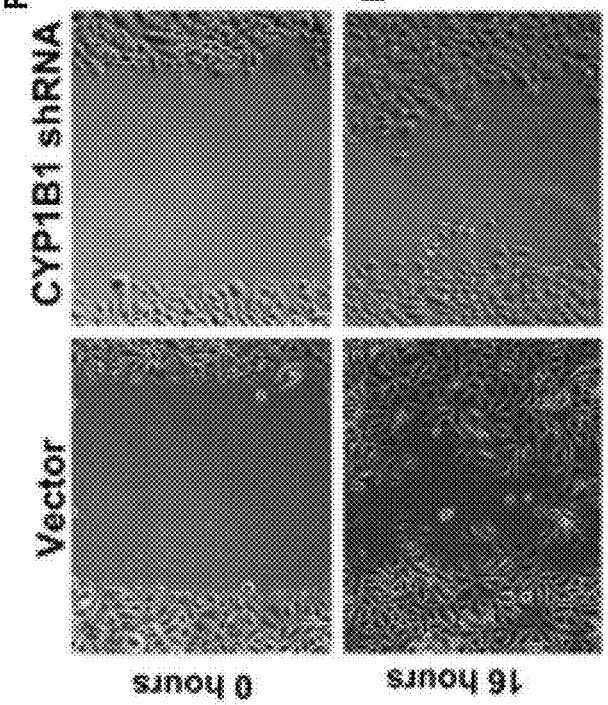
Fig. 1A.
Fig. 1B.
Fig. 1C.
Fig. 1D.
Fig. 1E.

Fig. 6A
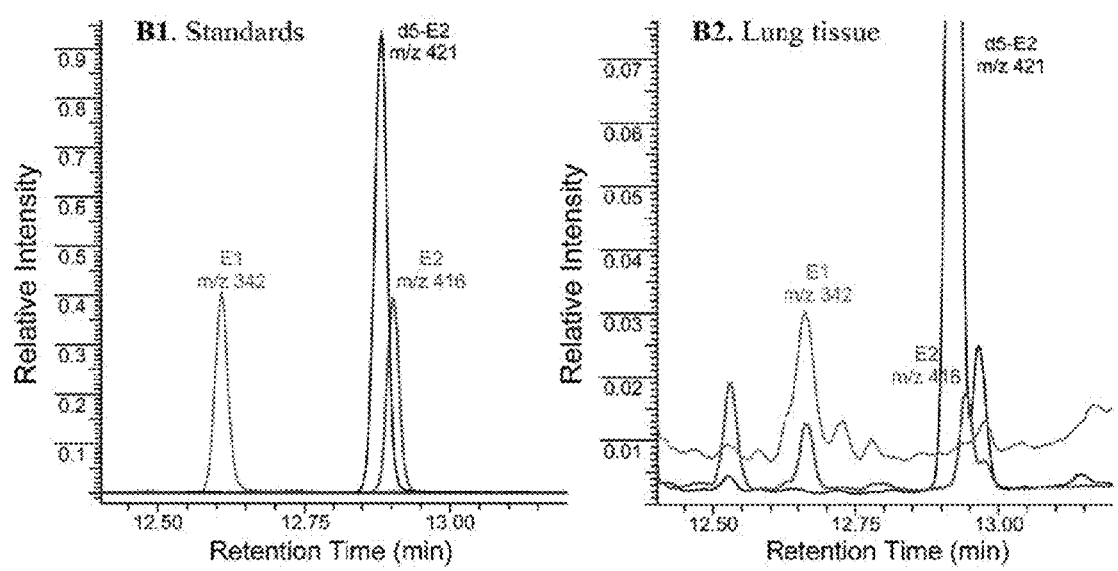
Fig. 6B

TARGETING OF CYP1B1 IN THE TREATMENT OF HEAD AND NECK CANCER AND LUNG CANCER

CROSS REFERENCE TO RELATED APPLICATIONS

This application is the U.S. National Phase of PCT Application No. PCT/US2011/062639, filed on Nov. 30, 2011, and claims priority to U.S. Provisional Application No. 61/418,075 filed on Nov. 30, 2010, the contents of each application are incorporated by reference herein, in their entirety and for all purposes.

STATEMENT OF GOVERNMENT SUPPORT

The inventions described herein were made, in part, with funds obtained from the National Cancer Institute, Grant Nos. CA-006927, CA-96310, CA-118114, CA-125152, and CA-113451. The U.S. government may have certain rights in these inventions.

FIELD OF THE INVENTION

The invention relates generally to the field of cancer treatment. More particularly, the invention relates to methods for treating cancers such as head and neck cancer and lung cancer by inhibiting the expression or biologic activity of CYP1B1.

BACKGROUND OF THE INVENTION

Various publications, including patents, published applications, technical articles and scholarly articles are cited throughout the specification. Each of these cited publications is incorporated by reference herein, in its entirety and for all purposes.

Lung cancer is a leading cause of cancer death in the United States and has surpassed breast cancer as the primary cause of cancer-related mortality in women. Exposure to tobacco smoke is estimated to account for approximately 90% of all lung cancers. Women appear to have an increased susceptibility to tobacco carcinogens but have a better prognosis after lung cancer diagnosis as compared with men. Estrogens may affect the susceptibility of women to lung cancer.

Head and neck cancer, currently the sixth most common cancer in the U.S., accounts for 650,000 new cancer cases each year worldwide. Head and neck cancer is a heterogeneous group of malignancies that develop primarily in the squamous epithelium of the lip, oral cavity, pharynx, larynx, nasal cavity, and paranasal sinuses. A rise in the incidence of squamous cell carcinoma (SCC) of the head and neck (HNSCC) in adults age 40 or less has been reported and attributed primarily to an increase in the prevalence of tongue cancers.

Exposure to tobacco smoke is among the major risk factors for developing lung cancer or HNSCC. It is well documented that the majority of non-smoking and non-drinking lung cancer patients are females. Recent data suggest that 75% of young, non-smoker/non-drinker HNSCC patients who develop oral tongue SCC (not associated with human papilloma virus infection) are female. Thus, in addition to the major risk factors, female hormones may contribute to head and neck carcinogenesis.

CYP1B1 is an enzyme that, along with CYP1A1 and CYP3A4, catalyzes the formation of carcinogenic metabolites of 17β-estradiol (E2) and of constituents of tobacco smoke that are subsequently inactivated by one or more detoxification enzymes, including catechol-o-methyltransferase (COMT), sulfotransferase (SULT)1A1, UDP-glucuronosyltransferase (UGT)1A1 and glutathione-S-transferase (GST)P1.

There is a need for additional treatments for head and neck cancers and for lung cancers, including chemopreventive therapies.

SUMMARY OF THE INVENTION

The invention features methods for inhibiting the motility or the proliferation of a premalignant cell or a malignant cell. Generally, the methods comprise inhibiting the expression of the CYP1B1 gene or inhibiting the biologic activity of the CYP1B1 protein in the premalignant cell or the malignant cell such that the motility or proliferation of the cell is consequentially inhibited. Inhibiting the expression of the CYP1B1 gene may comprise using RNA interference, modulating miRNA, or exposing cells having the CYP1B1 gene to a compound that inhibits CYP1B1 gene expression. For example, inhibiting CYP1B1 gene expression may comprise transforming the premalignant cell or the malignant cell with a nucleic acid molecule that interferes with the expression of the CYP1B1 gene. Inhibiting CYP1B1 gene expression may comprise contacting a cell having the CYP1B1 gene with a compound that inhibits CYP1B1 gene expression, a non-limiting example of which is resveratrol 2,4,3',5'-tetramethoxystilbene, which may suppress CYP1B1 mRNA levels. Inhibiting the biologic activity of the CYP1B1 protein comprises contacting the premalignant cell or the malignant cell with an effective amount of a compound or biomolecule that inhibits the biologic activity of the CYP1B1 protein.

In preferred aspects, the premalignant cell or the malignant cell may be a cell of the head and neck or of the lung. The cell of the head and neck may be a squamous epithelial cell of the lip, oral cavity, pharynx, larynx, nasal cavity, or paranasal sinuses, and may be a squamous cell carcinoma of the head and neck. The cell of the head and neck may be a mucoepidermoid carcinoma cell, adenoid cystic carcinoma cell, adenocarcinoma cell, small-cell undifferentiated cancer cell, esthesioneuroblastoma cell, Hodgkin lymphoma cell, or a Non-Hodgkin lymphoma cell. The cell of the lung may be a small cell lung cancer cell or a non-small cell lung cancer cell. The premalignant cell of the lung may comprise atypical adenomatous hyperplasia.

The nucleic acid molecule that interferes with the expression of the CYP1B1 gene may comprise a RNAi molecule, for example, a shRNA or miRNA that specifically hybridizes with CYP1B1 mRNA, particularly under stringent conditions. The compound that inhibits CYP1B1 biologic activity may comprise, but is not limited to, a polyphenol. For example, the compound may comprise a flavonoid such as, but not limited to, homoeriodictyol, or may comprise a stilbene such as, but not limited to, resveratrol 2,4,3',5'-tetramethoxystilbene, or a derivative thereof. The biomolecule that inhibits CYP1B1 biologic activity may comprise, but is not limited to, an antibody that specifically binds to CYP1B1.

The invention also features methods for treating or preventing a malignancy of the head and neck, and for treating a malignancy of the lung. The methods comprise administering to a subject in need thereof a nucleic acid molecule that interferes with the expression of the CYP1B1 gene, wherein the nucleic acid molecule transforms a malignant cell of the head and neck, or transforms a malignant cell of the lung, and interferes with the expression of the CYP1B1 gene in the transformed cell. Alternatively, the methods comprise administering to a subject in need thereof an effective amount of a compound that inhibits the biologic activity of the CYP1B1 protein in a malignant cell of the head and neck, or a malignant cell of the lung.

The malignant cell of the head and neck may be a squamous epithelial cell of the lip, oral cavity, pharynx, larynx, nasal cavity, or paranasal sinuses, and may be a squamous cell carcinoma of the head and neck. The malignant cell of the head and neck may be a mucoepidermoid carcinoma cell, adenoid cystic carcinoma cell, adenocarcinoma cell, small-cell undifferentiated cancer cell, esthesioneuroblastoma cell, Hodgkin lymphoma cell, or a Non-Hodgkin lymphoma cell. The malignant cell of the lung may be a small cell lung cancer cell or a non-small cell lung cancer cell. The subject can be any animal, preferably is a mammal, and most preferably is a human being.

The nucleic acid molecule that interferes with the expression of the CYP1B1 gene may comprise a RNAi molecule, for example, a shRNA or miRNA that specifically hybridizes with CYP1B1 mRNA, particularly under stringent conditions. The compound that inhibits CYP1B1 gene expression, CYP1B1 protein levels, or CYP1B1 biologic activity may comprise, but is not limited to, a polyphenol. For example, the compound may comprise a flavonoid such as, but not limited to, homoeriodictyol, or may comprise a stilbene such as, but not limited to, resveratrol 2,4,3',5'-tetramethoxystilbene, or a derivative thereof.

BRIEF DESCRIPTION OF THE DRAWINGS

FIGS. 1A-1E show that CYP1B1 deficiency decreases the motility of MSK-Leuk1 cells. FIG. 1A shows the detection of CYP1B1 in vector-expressing and shRNA-expressing cells by Western blot. Stable clones were selected with puromycin for 1 week, and expanded and analyzed using antibodies specific for CYP1B1. FIG. 1B shows representative images of cell monolayers at baseline (0 hours) and 16 hours post-scratch, treated with vehicle (0.01% ethanol) or E2 (1 nM). A similar response was observed for vehicle- and E2-treated cells. FIG. 1C shows a percentage of gap closure calculated as (area at 16 h-area at 0 h)/(area at 0 h) in CYP1B1 shRNA-expressing cells and vector-expressing cells treated with vehicle or E2. Gap area was calculated as a mean of 3 replicates. FIG. 1D shows apoptosis in CYP1B1 shRNA-expressing cells and vector-expressing cells during the 16-h period, as measured using a Nexin kit (Millipore). FIG. 1E shows proliferation of CYP1B1 shRNA-expressing cells and vector-expressing cells during the 16-h period, measured using a Fluorescent DNA Quantitation kit (BioRad). All bars represent the mean of 3 replicates ±standard error.

FIG. 2A shows that CYP1B1 deficiency inhibits proliferation of MSK-Leuk1 cells (total DNA). FIG. 2B shows that exposure to E2 inhibits apoptosis of MSK-Leuk1 cells (annexin). FIG. 2C shows that Fulvestrant (1 µM) restores E2-mediated decrease of apoptosis in MSK-Leuk1 cells. All bars represent the mean of 3 replicates ±standard error.

FIG. 3A shows a Venn diagram showing the distribution of differentially expressed genes (P<0.001) between control lungs and lungs exposed to smoke for 3, 8, and 20 weeks. The 10 genes depicted in Group A are modulated to all three time points. Groups B to D correspond to genes in common between 3 and 8 weeks (B), 3 and 20 weeks (C), and 8 and 20 weeks (D), whereas Groups E to G represent genes identified only at 3 weeks (E), 8 weeks (F), or 20 weeks (G). The genes represented in each group are listed in Table 1. FIG. 3B shows a heat map representing the median normalized expression values for the 10 genes altered at all three time points. Data for technical (same letter, e.g., aa) and biological (different letters, e.g., ab) replicates are included.

FIG. 6A and FIG. 6B show the detection of estrogens within murine lung tissue. Lung tissue from female A/J mice was subjected to immunohistochemical and GC/MS analyses. FIG. 6A shows detection of E2, ERα, and ERβ in lung epithelial cells by immunostaining. The bronchioloalveolar epithelium (BAE) stained positive for all antigens evaluated. Subcellular staining was observed as follows: E2, strong nuclear and cytoplasmic staining in the BAE and some pneumocytes; ERα, cytoplasmic staining of the BAE; and ERβ, nuclear staining in the BAE and some pneumocytes. FIG. 6B shows selective ion monitoring of trimethylsilyl derivatives of E1 and E2 (1.1 pmol each) and d5-E2 (2.6 pmol) as standards (B1) and in the murine lung tissue (B2). Each trace represents different ions monitored. Deuterium-labeled E2 represents the internal standard. Unmarked peaks in B2 denote unknowns; the upper part of the chromatogram was cropped to enhance the visualization of small peaks.

DETAILED DESCRIPTION OF THE INVENTION

Figure 2A:
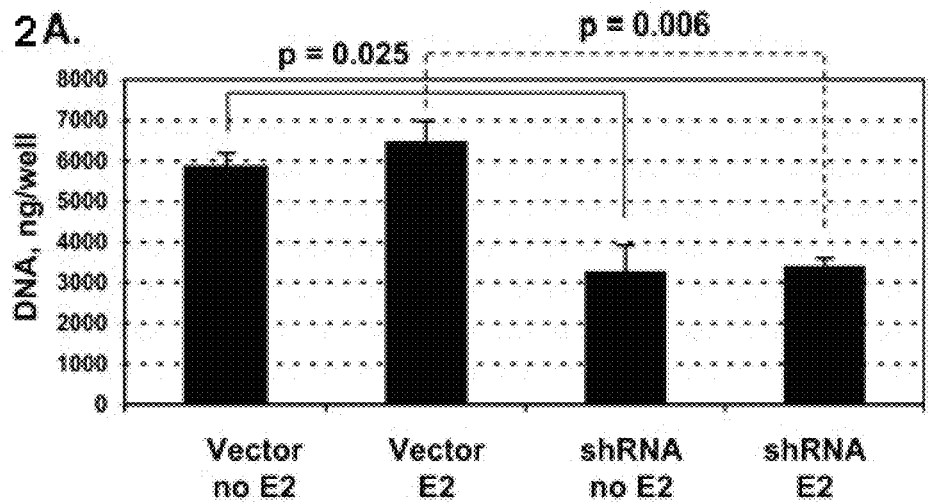
FIGS. 2A-2C show the effect of E2 and CYP1B1 on the proliferation and apoptosis of MSK-Leuk1 cells. Cells were incubated in phenol red-free and serum-free medium containing either 1 nM E2 or vehicle (0.01% ethanol) for 72 h.

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The term "about" as used herein when referring to a measurable value such as an amount encompasses variations of plus or minus 25%, 20%, 15%, 10%, 5%, 1%, 0.5%, 0.25%, or 0.1% from the specified value.

Premalignant or precancerous cells include cells that are not yet cancerous, but may become, or are likely to become cancerous.

Knockdown refers to reduced expression of a gene. A knockdown typically has at least about a 20% reduction in expression, preferably has at least about a 50% reduction in expression, and more preferably has at least about a 75% reduction in expression, and in some aspects has at least about an 80% to about an 85% reduction in expression, at least about an 85% to about a 90% reduction in expression, or about an 80% to about a 90% reduction in expression, and in some aspects has a greater than 90% reduction in expression, or a greater than 95% reduction in expression.

Transforming a cell comprises the introduction of exogenous or heterologous nucleic acid molecules into the cell according to any suitable technique in the art. Cells may be stably or transiently transformed.

Nucleic acid molecules include any chain of at least two nucleotides, which may be unmodified or modified RNA or DNA, hybrids of RNA and DNA, and may be single, double, or triple stranded.

The terms express, expressed, or expression of a nucleic acid molecule include the biosynthesis of a gene product. The terms encompass the transcription of a gene into RNA, the translation of RNA into a protein or polypeptide, and all naturally occurring post-transcriptional and post-translational modifications thereof.

Biomolecules include proteins, polypeptides, antibodies, nucleic acid molecules, lipids, monosaccharides, polysaccharides, and all fragments, analogs, homologs, conjugates, and derivatives thereof.

Inhibiting or interfering comprise reducing, decreasing, blocking, preventing, delaying, inactivating, desensitizing, stopping, knocking down (e.g., knockdown), and/or down-regulating the biologic activity or expression of a molecule or pathway of interest.

Biologic activity of CY1B1 includes, but is not limited to, enzymatic activity and metabolic activity. Some non-limiting specific examples of such activities are described throughout the specification.

It has been observed in accordance with the invention that exposure to tobacco smoke induces significant upregulation of cytochrome P450 1B1 (CYP1B1), an enzyme that metabolizes estrogens and certain chemical components of tobacco smoke, in lung tissue. Certain CYP1B1 metabolites are implicated in aspects of carcinogenesis. It has been further observed that the knockdown of CYP1B1 in precancerous head and neck epithelial cells inhibits their motility and proliferation. Motility has implications for the progression from premalignancy to malignancy, and may play a role in invasion and metastasis as cancer develops and progresses. Accordingly, the invention features various methods for inhibiting the motility or proliferation of premalignant and malignant cells, as well as methods for treating cancers of the lung or of the head and neck. The methods may be carried out in vivo or in vitro.

In some aspects, methods for inhibiting the motility of a premalignant cell or a malignant cell comprise inhibiting the expression of the CYP1B1 gene in the cell, for example, by transforming the premalignant cell or the malignant cell with a nucleic acid molecule that interferes with the expression of the CYP1B1 gene, or by contacting the premalignant cell or the malignant cell with a compound that interferes with the expression of the CYP1B1 gene, wherein inhibiting the expression of the CYP1B1 gene in the cell inhibits the motility of the premalignant cell or of the malignant cell. Inhibition of the expression of the CYP1B1 gene may comprise inhibition at the transcription or translation level.

In some aspects, methods for inhibiting the proliferation of a premalignant cell or a malignant cell comprise inhibiting the expression of the CYP1B1 gene in the cell, for example, by transforming the premalignant cell or the malignant cell with a nucleic acid molecule that interferes with the expression of the CYP1B1 gene, or by contacting the premalignant cell or the malignant cell with a compound that interferes with the expression of the CYP1B1 gene, wherein inhibiting the expression of the CYP1B1 gene in the cell inhibits the proliferation of the premalignant cell or of the malignant cell. Inhibition of the expression of the CYP1B1 gene may comprise inhibition at the transcription or translation level.

CYP1B1 expression can be inhibited through the use of a variety of post-transcriptional gene silencing (RNA silencing) techniques. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner. Levels of miRNA may be modulated in order to modulate the levels of CYB1B1 mRNA and decrease the levels of CYP1B1 protein. A CYP1B1 miRNA may comprise any of the miRNAs described by Tsuchiya Y et al. (2006) Cancer Res. 66:9090-8.

RNA interference (RNAi) is a mechanism of post-transcriptional gene silencing mediated by double-stranded RNA (dsRNA), which is distinct from antisense and ribozyme-based approaches. RNA interference is useful in a method involving inhibiting the expression of CYP1B1, for example, by administering a nucleic acid (e.g., dsRNA) that hybridizes under stringent conditions to the gene encoding CYP1B1, thereby attenuating its expression. RNA interference provides shRNA or siRNA that comprise multiple sequences that target one or more regions of the CYP1B1 gene. dsRNA molecules (shRNA or siRNA) are believed to direct sequence-specific degradation of mRNA in cells of various types after first undergoing processing by an RNase III-like enzyme called DICER into smaller dsRNA molecules comprised of two 21 nt strands, each of which has a 5' phosphate group and a 3' hydroxyl, and includes a 19 nt region precisely complementary with the other strand, so that there is a 19 nt duplex region flanked by 2 nt-3' overhangs. RNAi is thus mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides. In mammalian cells, dsRNA longer than approximately 30 nucleotides typically induces nonspecific mRNA degradation via the interferon response. However, the presence of siRNA in mammalian cells, rather than inducing the interferon response, results in sequence-specific gene silencing.

Viral vectors or DNA vectors encode short hairpin RNA (shRNA) which are processed in the cell cytoplasm to short interfering RNA (siRNA). In general, a short, interfering RNA (siRNA) comprises an RNA duplex that is preferably approximately 19 basepairs long and optionally further comprises one or two single-stranded overhangs or loops. An siRNA may comprise two RNA strands hybridized together, or may alternatively comprise a single RNA strand that includes a self-hybridizing portion. siRNAs may include one or more free strand ends, which may include phosphate and/or hydroxyl groups. siRNAs typically include a portion that hybridizes under stringent conditions with a target transcript. One strand of the siRNA (or, the self-hybridizing portion of the siRNA) is typically precisely complementary with a region of the target transcript, meaning that the siRNA hybridizes to the target transcript without a single mismatch. In aspects in which perfect complementarity is not achieved, it is generally preferred that any mismatches be located at or near the siRNA termini.

siRNAs have been shown to downregulate gene expression when transferred into mammalian cells by such methods as transfection, electroporation, cationic liposome-mediated transfection, or microinjection, or when expressed in cells via any of a variety of plasmid-based approaches. The siRNA may include two individual nucleic acid strands or of a single strand with a self-complementary region capable of forming a hairpin (stem-loop) structure. A number of variations in structure, length, number of mismatches, size of loop, identity of nucleotides in overhangs, etc., are consistent with effective siRNA-triggered gene silencing. While not wishing to be bound by any theory, it is believed that intracellular processing (e.g., by DICER) of a variety of different precursors results in production of siRNA capable of effectively mediating gene silencing. Generally, it is preferred to target exons rather than introns, and it may also be preferable to select sequences complementary to regions within the 3' portion of the target transcript. Generally, it is preferred to select sequences that contain approximately an equimolar ratio of the different nucleotides and to avoid stretches in which a single residue is repeated multiple times.

siRNAs may thus comprise RNA molecules having a double-stranded region approximately 19 nucleotides in length with 1-2 nucleotide 3' overhangs on each strand, resulting in a total length of between approximately 21 and 23 nucleotides. siRNAs also include various RNA structures that may be processed in vivo to generate such molecules. Such structures include RNA strands containing two complementary elements that hybridize to one another to form a stem, a loop, and optionally an overhang, preferably a 3' overhang. Preferably, the stem is approximately 19 bp long, the loop is about 1-20, more preferably about 4-10, and most preferably about 6-8 nt long and/or the overhang is about 1-20, and more preferably about 2-15 nt long. In certain aspects, the stem is minimally 19 nucleotides in length and may be up to approximately 29 nucleotides in length. Loops of 4 nucleotides or greater are less likely subject to steric constraints than are shorter loops and therefore may be preferred. The overhang may include a 5' phosphate and a 3' hydroxyl. The overhang may, but need not comprise a plurality of U residues, e.g., between 1 and 5 U residues. Classical siRNAs as described above trigger degradation of mRNAs to which they are targeted, thereby also reducing the rate of protein synthesis. In addition to siRNAs that act via the classical pathway, certain siRNAs that bind to the 3' UTR of a template transcript may inhibit expression of a protein encoded by the template transcript by a mechanism related to but distinct from classic RNA interference, e.g., by reducing translation of the transcript rather than decreasing its stability. Such RNAs are referred to as microRNAs (miRNAs) and are typically between approximately 20 and 26 nucleotides in length, e.g., 22 nt in length. Chunsheng L et al. (2009) AAPS J. 11:747-57. It is believed that they are derived from larger precursors known as small temporal RNAs (stRNAs) or mRNA precursors, which are typically approximately 70 nt long with an approximately 4-15 nt loop. Endogenous RNAs of this type have been identified in a number of organisms including mammals, suggesting that this mechanism of post-transcriptional gene silencing may be widespread. MicroRNAs have been shown to block translation of target transcripts containing target sites.

siRNAs such as naturally occurring or artificial (i.e., designed by humans) mRNAs that bind within the 3' UTR (or elsewhere in a target transcript) and inhibit translation may tolerate a larger number of mismatches in the siRNA/template duplex, and particularly may tolerate mismatches within the central region of the duplex. In fact, there is evidence that some mismatches may be desirable or required as naturally occurring stRNAs frequently exhibit such mismatches as do mRNAs that have been shown to inhibit translation in vitro. For example, when hybridized with the target transcript such siRNAs frequently include two stretches of perfect complementarity separated by a region of mismatch. A variety of structures are possible. For example, the mRNA may include multiple areas of nonidentity (mismatch). The areas of nonidentity (mismatch) need not be symmetrical in the sense that both the target and the mRNA include nonpaired nucleotides. Typically the stretches of perfect complementarity are at least 5 nucleotides in length, e.g., 6, 7, or more nucleotides in length, while the regions of mismatch may be, for example, 1, 2, 3, or 4 nucleotides in length.

Hairpin structures designed to mimic siRNAs and mRNA precursors are processed intracellularly into molecules capable of reducing or inhibiting expression of target transcripts. These hairpin structures, which are based on classical siRNAs consisting of two RNA strands forming a 19 bp duplex structure are classified as class I or class II hairpins. Class I hairpins incorporate a loop at the 5' or 3' end of the antisense siRNA strand (i.e., the strand complementary to the target transcript whose inhibition is desired) but are otherwise identical to classical siRNAs. Class II hairpins resemble mRNA precursors in that they include a 19 nt duplex region and a loop at either the 3' or 5' end of the antisense strand of the duplex in addition to one or more nucleotide mismatches in the stem. These molecules are processed intracellularly into small RNA duplex structures capable of mediating silencing. They appear to exert their effects through degradation of the target mRNA rather than through translational repression as is thought to be the case for naturally occurring mRNAs and stRNAs.

Thus, a diverse set of RNA molecules containing duplex structures is able to mediate silencing through various mechanisms. Any such RNA, one portion of which binds to a target transcript and reduces its expression, whether by triggering degradation, by inhibiting translation, or by other means, may be considered an siRNA, and any structure that generates such an siRNA (i.e., serves as a precursor to the RNA) is useful.

A further method of RNA interference is the use of short hairpin RNAs (shRNA). A plasmid containing a DNA sequence encoding a particular desired siRNA sequence is delivered into a target cell via transfection or virally-mediated infection. Once in the cell, the DNA sequence is continuously transcribed into RNA molecules that loop back on themselves and form hairpin structures through intramolecular base pairing. These hairpin structures, once processed by the cell, are equivalent to transfected siRNA molecules and are used by the cell to mediate RNAi of the desired protein. The use of shRNA has an advantage over siRNA transfection as the former can lead to stable, long-term inhibition of protein expression. Inhibition of protein expression by transfected siRNAs is a transient phenomenon that does not occur for time periods longer than several days. In some cases, though, this may be preferable and desired. In cases where longer periods of protein inhibition are necessary, shRNA mediated inhibition is preferable. The use of shRNA is particularly preferred. Typically, siRNA-encoding vectors are constructs comprising a promoter, a sequence of the target gene to be silenced in the sense orientation, a spacer, the antisense of the target gene sequence, and a terminator.

Inhibition of the expression of CYP1B1 can also be effectuated by other means that are known and readily practiced in the art. For example, antisense nucleic acids can be used. Antisense RNA transcripts have a base sequence complementary to part or all of any other RNA transcript in the same cell. Such transcripts modulate gene expression through a variety of mechanisms including the modulation of RNA splicing, the modulation of RNA transport and the modulation of the translation of mRNA. Accordingly, in certain aspects, inhibition of the CYP1B1 protein in a cell can be accomplished by expressing an antisense nucleic acid molecule in the cell.

Antisense nucleic acids are generally single-stranded nucleic acids (DNA, RNA, modified DNA, or modified RNA) complementary to a portion of a target nucleic acid (e.g., an mRNA transcript) and therefore able to bind to the target to form a duplex. Typically, they are oligonucleotides that range from 15 to 35 nucleotides in length but may range from 10 up to approximately 50 nucleotides in length. Binding typically reduces or inhibits the expression of the target nucleic acid, such as the gene encoding CYP1B1. For example, antisense oligonucleotides may block transcription when bound to genomic DNA, inhibit translation when bound to mRNA, and/or lead to degradation of the nucleic acid. Inhibition of the expression of the CYP1B1 protein can be achieved by the administration of antisense nucleic acids comprising sequences complementary to those of the mRNA that encodes the CYP1B1 protein.

Antisense oligonucleotides can be synthesized with a base sequence that is complementary to a portion of any RNA transcript in the cell. Antisense oligonucleotides can modulate gene expression through a variety of mechanisms including the modulation of RNA splicing, the modulation of RNA transport and the modulation of the translation of mRNA. Various properties of antisense oligonucleotides including stability, toxicity, tissue distribution, and cellular uptake and binding affinity may be altered through chemical modifications including (i) replacement of the phosphodiester backbone (e.g., peptide nucleic acid, phosphorothioate oligonucleotides, and phosphoramidate oligonucleotides), (ii) modification of the sugar base (e.g., 2'-O-propylribose and 2'-methoxyethoxyribose), and (iii) modification of the nucleoside (e.g., C-5 propynyl U, C-5 thiazole U, and phenoxazine C).

Inhibition of CYP1B1 can also be effectuated by use of ribozymes. Certain nucleic acid molecules referred to as ribozymes or deoxyribozymes have been shown to catalyze the sequence-specific cleavage of RNA molecules. The cleavage site is determined by complementary pairing of nucleotides in the RNA or DNA enzyme with nucleotides in the target RNA. Thus, RNA and DNA enzymes can be designed to cleave to any RNA molecule, thereby increasing its rate of degradation.

In some aspects, the cells can be specifically transformed with transcription-silencing nucleic acids such as shRNA or siRNA, or can be transformed with vectors encoding such nucleic acids such that the cell expresses the inhibitory nucleic acid molecules. Transformation of the cells can be carried out according to any means suitable in the art.

A cell can be transformed with such nucleic acid molecules according to any means available in the art such as those describe or exemplified herein. It is preferred that cells are stably transformed with a vector comprising a nucleic acid sequence encoding such regulatory nucleic acid molecules, although transiently transformations are suitable. Any vector suitable for transformation of the particular cell of interest can be used. In preferred embodiments, the vector is a viral vector. In some embodiments, the viral vector is a lentivirus vector.

In some aspects, methods for inhibiting the motility of a premalignant cell or a malignant cell comprise inhibiting the biologic activity of the CYP1B1 protein in the premalignant cell or the malignant cell, for example, by contacting the premalignant cell or the malignant cell with an effective amount of a compound or biomolecule that inhibits the biologic activity of the CYP1B1 protein in the cell, wherein inhibiting the biologic activity of the CYP1B1 protein in the cell inhibits the motility of the premalignant cell or of the malignant cell. Biologic activity of the CYP1B1 protein comprises, among other things, metabolism of estrogens and the metabolism of components of tobacco smoke such as polycyclic aromatic hydrocarbons. The estrogen may be natural or synthetic, may be an estrogen hormone, including estradiol (E2), estriol (E3), estrone (E1), may be a phytoestrogen, may be a mycoestrogen, may be a xenoestrogen, or any combination thereof.

In some aspects, methods for inhibiting the proliferation of a premalignant cell or a malignant cell comprise inhibiting the biologic activity of the CYP1B1 protein in the premalignant cell or the malignant cell, for example, by contacting the premalignant cell or the malignant cell with an effective amount of a compound or biomolecule that inhibits the biologic activity of the CYP1B1 protein in the cell, wherein inhibiting the biologic activity of the CYP1B1 protein in the cell inhibits the proliferation of the premalignant cell or of the malignant cell. Biologic activity of the CYP1B1 protein comprises, among other things, metabolism of estrogens and the metabolism of components of tobacco smoke such as polycyclic aromatic hydrocarbons.

The compound that inhibits the biologic activity of the CYP1B1 protein may comprise a polyphenol, for example, a polyphenol that inhibits the biologic activity of CYP1B1. Polyphenols that inhibit the biologic activity include, but are not limited to flavonoids and stilbenes. Thus, the compound that inhibits the biologic activity of the CYP1B1 protein may comprise, but is not limited to, a flavonoid, including hesperidin, hesperetin, diosmetin, diosmin, eriodictyol, or homoeriodictyol, or any metabolite or derivative thereof. The compound that inhibits the biologic activity of the CYP1B1 protein may comprise, but is not limited to, a stilbene, including resveratrol, or an analog of resveratrol such as resveratrol 2,4,3',5'-tetramethoxystilbene, or any derivative thereof. A biomolecule that inhibits the biologic activity of the CYP1B1 protein may comprise an antibody that specifically binds to CYP1B1, see for example, Gribben J G et al. (2005) Clin. Cancer Res. 11:4430-6.

In an alternative aspect, methods for inhibiting the motility or proliferation of a premalignant cell or a malignant cell comprise inhibiting the biologic activity of a substrate of the CYP1B1 protein in the premalignant cell or the malignant cell, for example, by contacting the premalignant cell or the malignant cell with an effective amount of a compound or biomolecule that inhibits the biologic activity of the substrate of the CYP1B1 protein, wherein inhibiting the biologic activity of the substrate of the CYP1B1 protein inhibits the motility of the premalignant cell or of the malignant cell. Substrates of the CYP1B1 protein comprises, among other things, estrogens and components of tobacco smoke such as polycyclic aromatic hydrocarbons.

The methods for inhibiting the motility or proliferation of cells may be carried out on any premalignant or malignant cell that is motile or capable of becoming motile, or is proliferating or capable of proliferating. For example, the premalignant cells or the malignant cells may be epithelial cells. In some aspects, the premalignant cells or the malignant cells are cells of the head and neck. Non-limiting examples of cells of the head and neck include squamous epithelial cells of the lip, oral cavity, pharynx, larynx, nasal cavity, or paranasal sinuses, as well as a mucoepidermoid carcinoma cells, adenoid cystic carcinoma cells, adenocarcinoma cells, small-cell undifferentiated cancer cells, esthesioneuroblastoma cells, Hodgkin lymphoma cells, and Non-Hodgkin lymphoma cells. In some aspects, the premalignant cells or the malignant cells are cells of the lung. Non-limiting examples of lung malignancies include small cell lung cancer and non small cell lung cancer, and the lung cells may be premalignant or malignant with any of these lung cancer types. Non-limiting examples of non small cell lung cancers include squamous cell carcinoma of the lung, adenocarcinoma, adenoma, bronchioalveolar carcinoma, and large-cell undifferentiated carcinoma.

The invention also features methods for treating, preventing, or inhibiting malignancies. In some aspects, the methods may be used to inhibit premalignant cells from progressing to a malignant state, or to reduce or substantially reduce the amount of premalignant cells that progress to a malignant state, and/or the rate at which premalignant cells progress to a malignant state. Preferred malignancies that can be prevented or treated using the methods include malignancies of the head and neck and malignancies of the lung. It is contemplated, though, that any malignancy that is caused by, facilitated by, is advanced by, is enhanced by, or is otherwise made worse by the expression of the CYP1B1 gene or the biologic activity of the CYP1B1 protein can be treated or prevented with the methods.

In some aspects, a method for treating or preventing a malignancy of the head and neck comprises administering to a subject in need thereof a nucleic acid molecule or a compound that interferes with the expression of the CYP1B1 gene. Inhibition of the expression of the CYP1B1 gene may be at the transcriptional or translational level. The nucleic acid molecule or the compound may be administered in any effective concentration. The nucleic acid molecule may be administered as comprised in any suitable vector, including those described or exemplified herein. The nucleic acid molecule may be specifically targeted to malignant cells through any delivery system suitable in the art. Administering the nucleic acid molecule may comprise transforming a premalignant or malignant cell of the head and neck in the subject with the nucleic acid molecule or vector comprising the nucleic acid molecule. Thus, transforming a premalignant cell or a malignant cell of the head and neck with the nucleic acid molecule interferes with the expression of the CYP1B1 gene in the transformed cell. The nucleic acid molecule preferably is a RNAi molecule, and more preferably is a shRNA or miRNA that specifically hybridizes with CYP1B1 mRNA in the cell. The compound may comprise a stilbene such as resveretrol 2,4,3',5'-tetramethoxystilbene, and the compound may be present in a composition comprising the compounds and an acceptable carrier. Interfering with the expression of the CYP1B1 gene may, for example, inhibit motility or proliferation of the cell, and also may inhibit the metabolism of an estrogen or the metabolism of components of tobacco smoke such as polycyclic aromatic hydrocarbons.

In some aspects, a method for treating or preventing a malignancy of the head and neck comprises administering to a subject in need thereof one or more nucleic acid molecules or compounds that interfere with the expression of one or more genes that is/are differentially expressed in a head and neck cell when the subject is exposed to an amount of tobacco smoke sufficient to cause differential expression of the one or more genes. Preferred examples of differentially expressed genes include, but are not limited to, CYP1B1, CRY1, CBR3, UGT1A6, AU018778, EG245174, CES3, TEF, HDC, and COL3A1.

The one or more nucleic acid molecules or compounds may be administered in any effective concentration. The one or more nucleic acid molecules may be administered as comprised in any suitable vector, including those described or exemplified herein. The compound may be administered as a composition in which it is mixed with an acceptable carrier, which may be water, saline, balanced salt solution, or other suitable carrier known in the art. The one or more nucleic acid molecules or compound may be specifically targeted to malignant cells through any delivery system suitable in the art. Administering the one or more nucleic acid molecules may comprise transforming a premalignant or malignant cell of the head and neck in the subject with the one or more nucleic acid molecule or vector comprising the one or more nucleic acid molecule. Thus, transforming a premalignant cell or a malignant cell of the head and neck with the one or more nucleic acid molecules interferes with the expression of the gene(s) of interest that is/are differentially expressed when the subject is exposed to an amount of tobacco smoke sufficient to cause differential expression of the gene(s) in the transformed cell. The one or more nucleic acid molecules preferably is/are a RNAi molecule, and more preferably is/are a shRNA or miRNA that specifically hybridizes with CYP1B1, CRY1, CBR3, UGT1A6, AU018778, EG245174, CES3, TEF, HDC, or COL3A1 mRNA in the cell, although it should be noted that these mRNA are non-limiting examples of differentially expressed genes.

In some aspects, a method for treating or preventing a malignancy of the lung comprises administering to a subject in need thereof a nucleic acid molecule that interferes with the expression of the CYP1B1 gene. The nucleic acid molecule may be administered in any effective concentration. The nucleic acid molecule may be administered as comprised in any suitable vector, including those described or exemplified herein. The nucleic acid molecule may be specifically targeted to malignant cells through any delivery system suitable in the art. Administering the nucleic acid molecule may comprise transforming a premalignant or malignant cell of the lung in the subject with the nucleic acid molecule or vector comprising the nucleic acid molecule. Thus, transforming a premalignant cell or a malignant cell of the lung with the nucleic acid molecule interferes with the expression of the CYP1B1 gene in the transformed cell. The nucleic acid molecule preferably is a RNAi molecule, and more preferably is a shRNA that specifically hybridizes with CYP1B1 mRNA in the cell. Interfering with the expression of the CYP1B1 gene may, for example, inhibit motility or proliferation of the cell, and also may inhibit the metabolism of an estrogen or the metabolism of components of tobacco smoke such as polycyclic aromatic hydrocarbons.

In some aspects, a method for treating or preventing a malignancy of the lung comprises administering to a subject in need thereof one or more nucleic acid molecules or compounds that interfere with the expression of one or more genes that is/are differentially expressed in a lung cell when the subject is exposed to an amount of tobacco smoke sufficient to cause differential expression of the gene(s). Preferred examples of differentially expressed genes include, but are not limited to, CYP1B1, CRY1, CBR3, UGT1A6, AU018778, EG245174, CES3, TEF, HDC, and COL3A1. CYP1B1 and CRY1 are more preferred.

The one or more nucleic acid molecules may be administered in any effective concentration. The one or more nucleic acid molecules may be administered as comprised in any suitable vector, including those described or exemplified herein. The one or more nucleic acid molecules may be specifically targeted to malignant cells through any delivery system suitable in the art. Administering the nucleic acid molecule may comprise transforming a premalignant or malignant cell of the lung in the subject with the one or more nucleic acid molecules or vector comprising the one or more nucleic acid molecules. Thus, transforming a premalignant cell or a malignant cell of the lung with the nucleic acid molecule interferes with the expression of the one or more genes of interest that is/are differentially expressed when the subject is exposed to an amount of tobacco smoke sufficient to cause differential expression of the gene(s) in the transformed cell. The one or more nucleic acid molecules preferably is/are a RNAi molecule, and more preferably is/are a shRNA that specifically hybridizes with CYP1B1, CRY1, CBR3, UGT1A6, AU018778, EG245174, CES3, TEF, HDC, or COL3A1 mRNA in the cell.

In some aspects, a method for treating or preventing a malignancy of the lung or a malignancy of the head and neck comprises modulating in a subject in need thereof the expression of one or more genes that is/are differentially expressed in a lung cell or a head and neck cell when the subject is exposed to an amount of tobacco smoke sufficient to cause differential expression of the one or more genes, or that is differentially expressed in a lung cell or a head and neck cell during tumor formation. Preferred examples of differentially expressed genes include, but are not limited to, CYP1B1, CRY1, CBR3, UGT1A6, AU018778, EG245174, CES3, TEF, HDC, and COL3A1. CYP1B1 and CRY1 are more preferred. Modulating gene expression may comprise enhancing the expression of the one or more genes, and may comprise diminishing expression of the one or more genes. Modulating gene expression may be accomplished according to any technique suitable in the art, including those described or exemplified herein.

In some preferred aspects, a method for treating or preventing a malignancy of the lung or a malignancy of the head and neck comprises modulating in a subject in need thereof the expression of the CRY1 (cryptochrome 1) gene in a lung cell or a head and neck cell of the subject. Modulating the expression of CRY1 may, among other things, modulate the circadian rhythm of the lung cancer cells or head and neck cancer cells, and preferably restore the circadian rhythm of the lung cancer cells or head and neck cancer cells.

In some aspects, a method for treating or preventing a malignancy of the head and neck comprises administering to a subject in need thereof an effective amount of a compound that inhibits the biologic activity of the CYP1B1 protein in a malignant cell of the head and neck. The compound may be specifically targeted to malignant cells through any delivery system suitable in the art. The compound that inhibits the biologic activity of the CYP1B1 protein may be a polyphenol that inhibits the biologic activity of the CYP1B1 protein. In some aspects, the polyphenol may comprise, but is not limited to, a flavonoid, including hesperidin, hesperetin, diosmetin, diosmin, eriodictyol, or homoeriodictyol, or any metabolite or derivative thereof. In some aspects, the polyphenol may comprise, but is not limited to, a stilbene, including resveratrol, or an analog of resveratrol such as resveratrol 2,4,3',5'-tetramethoxystilbene, or any derivative thereof. As an alternative to the compound, a biomolecule that inhibits the biologic activity of the CYP1B1 protein in a malignant cell of the head and neck may be used. Interfering with the biologic activity of the CYP1B1 protein may, for example, inhibit motility or proliferation of the cell, and also may inhibit the metabolism of an estrogen or the metabolism of components of tobacco smoke such as polycyclic aromatic hydrocarbons.

In some aspects, a method for treating or preventing a malignancy of the lung comprises administering to a subject in need thereof an effective amount of a compound that inhibits the biologic activity of the CYP1B1 protein in a malignant cell of the lung. The compound may be specifically targeted to malignant cells through any delivery system suitable in the art. The compound that inhibits the biologic activity of the CYP1B1 protein may be, but is not limited to, a polyphenol that inhibits the biologic activity of the CYP1B1 protein. In some aspects, the polyphenol may comprise, but is not limited to, a flavonoid, including hesperidin, hesperetin, diosmetin, diosmin, eriodictyol, or homoeriodictyol, or any metabolite or derivative thereof. In some aspects, the polyphenol may comprise, but is not limited to, a stilbene, including resveratrol, or an analog of resveratrol such as resveratrol 2,4,3',5'-tetramethoxystilbene, or any derivative thereof. As an alternative to the compound, a biomolecule that inhibits the biologic activity of the CYP1B1 protein in a malignant cell of the lung may be used. Interfering with the biologic activity of the CYP1B1 protein may, for example, inhibit motility or proliferation of the cell, and also may inhibit the metabolism of an estrogen or the metabolism of components of tobacco smoke such as polycyclic aromatic hydrocarbons.

In some aspects, a method for treating or preventing a malignancy of the lung or of the head and neck comprises inhibiting in the lung or in the head and neck of a subject in need thereof the expression of one or more genes encoding a protein that metabolizes an estrogen in the lung or the head and neck. The one or more genes may comprise a gene differentially expressed in the lung when the lung is exposed to tobacco smoke or during the process of tumor formation and/or a gene differentially expressed in the head and neck when the head and neck is exposed to tobacco smoke or during the process of tumor formation. Non-limiting examples of such genes are shown in FIGS. 3 and 5, and include CYP1B1, UGT1A1, and UGT1A6. The inhibiting step may comprise administering to the subject one or more nucleic acid molecules that interfere with the expression of the one or more genes. Administering the one or more nucleic acid molecules may comprise transforming a premalignant or malignant cell of the lung or of the head and neck in the subject with the one or more nucleic acid molecules or vector(s) comprising the one or more nucleic acid molecule. Thus, transforming a premalignant cell or a malignant cell of lung or of the head and neck interferes with the expression of the one or more genes in the premalignant or malignant cell. The nucleic acid molecule may be a RNA interference molecule such as a shRNA or a siRNA that specifically hybridizes under stringent conditions to the mRNA of the gene, for example, the mRNA of CYP1B1, UGT1A1, or UGT1A6.

In some aspects, a method for treating or preventing a malignancy of the lung or of the head and neck comprises administering to a subject in need thereof an effective amount of a compound that inhibits the biologic activity of a protein that synthesizes or metabolizes an estrogen in the lung or in the head and neck. The protein may be a protein differentially expressed in the lung when the lung is exposed to tobacco smoke or a protein differentially expressed in the head and neck when the head and neck are exposed to tobacco smoke. Non-limiting examples of such proteins include CYP1B1, UGT1A1, and UGT1A6. The compound may be a polyphenol such as a flavonoid or a stilbene. Non-limiting examples of suitable flavonoids include hesperidin, hesperetin, diosmetin, diosmin, eriodictyol, and homoeriodictyol. Non-limiting examples of suitable stilbenes include resveratrol 2,4,3', 5'-tetramethoxystilbene and derivatives thereof.

Any of the methods of treatment or prevention described or exemplified herein are suitable for use in any animal, with mammals being preferred. Non-limiting examples of mammals include mice, rats, rabbits, companion animals such as cats and dogs, farm animals, and primates. Human beings are most preferred.

Any malignant cell may be targeted and transformed according to the methods. Preferred examples of malignant cells are epithelial cells. For a malignancy of the head and neck, preferred epithelial cells include, without limitation, squamous epithelial cells of the lip, oral cavity, pharynx, larynx, nasal cavity, or paranasal sinuses, as well as a mucoepidermoid carcinoma cells, adenoid cystic carcinoma cells, adenocarcinoma cells, small-cell undifferentiated cancer cells, esthesioneuroblastoma cells, Hodgkin lymphoma cells, and Non-Hodgkin lymphoma cells. For a malignancy of the head and neck, preferred cells include any cells characterized as a squamous cell carcinoma of the head and neck. For a malignancy of the lung, preferred cells include any cells characterized as a small cell lung cancer, non small cell lung cancer, include squamous cell carcinoma of the lung, adenocarcinoma, adenoma, bronchioalveolar carcinoma, or large-cell undifferentiated carcinoma.

The following examples are provided to describe the invention in greater detail. They are intended to illustrate, not to limit, the invention.

Example 1

Knockdown of CYP1B1 Expression

Materials and Methods.

Cell lines and treatments. MSK-Leuk1 cells were derived from a dysplastic leukoplakia lesion located adjacent to a SCC of the tongue. MSK-Leuk1 cells were cultured in KGM medium (Lonza, Walkersville, Md.). MSK-Leuk1 cells (passage 33) were determined to be identical to the early passage MSK-Leuk1 cells (Identity Mapping Kit, Coriell Institute for Medical Research, Camden, N.J.). All HNSCC cell lines were derived from patients with SCC of the tongue. SCC9 (male) and SCC15 (male) cells were cultured in S-MEM medium, supplemented with 2 mM L-glutamine, 100 units/ml penicillin, 100 µg/ml streptomycin and 10% FBS. UPCI:SCC56 (male), UPCI:SCC103 (female) and UPCI:SCC122 (male) cells were cultured in MEM medium, supplemented with 2 mM L-glutamine, 100 µM non-essential amino acids, 50 µg/ml gentamycin (Gibco) and 10% FBS.

For all the experiments that involved estradiol (E2) exposure, MSK-Leuk1 cells were cultured in phenol red-free and serum-free DermaLife® K Medium (Lifeline Cell Technology, Walkersville, Md.). SCC cells were cultured in their respective media with no phenol red, supplemented with charcoal-stripped serum (Gibco, Carlsbad, Calif.). Cells were incubated for 48 h to remove endogenous estrogens and then plated at 70% confluence. After 24 h, the medium was replaced with either control medium containing vehicle (0.01% ethanol) or medium supplemented with 1 nM E2 (Sigma-Aldrich, St. Louis, Mo.). Cells were harvested after the appropriate treatment period and analyzed.

Generation of CYP1B1-deficient cell lines. A set of five lentivirus-encoded shRNA constructs specific for CYP1B1 (clone id TRCN0000062323-TRCN0000062327) and the empty pLKO.1 vector (control) were obtained from Open Biosystems (Huntsville, Ala.). Each of five constructs and the pLKO.1 vector were co-transfected along with the ViraPower Lentiviral Packaging Mix (Invitrogen, Carlsbad, Calif.) into 293FT producer cells, using Lipofectamine™2000 (Invitrogen, CA). The viral supernatants were harvested and viral titers ($10^5$-$10^6$ transduction units (TU)/ml) were determined using puromycin selection of normal human fibroblasts. MSK-Leuk1 cells were incubated with different dilutions of the viral supernatants and allowed to recover in complete medium. Transfection efficiency was estimated based on transfecting cells with a construct carrying green fluorescent protein and approached 100%. Stable clones were selected using puromycin (10 µg/ml, Sigma-Aldrich, St. Louis, Mo.) and analyzed for CYP1B1 levels by Western blot.

Cell motility assay. MSK-Leuk1 cells, expressing either vector or CYP1B1 shRNA, were cultured in phenol red-free and serum-free medium for 48 h and then plated at 70% confluence. After 24 h, the cells were treated with either vehicle or E2 (1 nM) in triplicate, as described above. When cells reached 100% confluence (48 h later), the surface of the cell culture dish was carefully scratched using a micropipette tip, thus making an evenly distributed gap in the cell monolayer. The medium was replaced, and five representative images of each gap were acquired at 0 h using a Nikon TE-2000U wide field inverted microscope (Optical Apparatus Co., Ardmore, Pa.) equipped with a Roper Scientific Cool Snap HQ camera. Another set of 5-10 representative images per gap was obtained following a 16-h incubation. The area devoid of cells was measured on every image using MetaMorph 7.0 (Molecular Devices, Inc., Sunnyvale, Calif.). The gap closure percentages were calculated as (area at 0 h–area at 16 h)/(area at 0 h).

In addition, a time-lapse movie capturing the process of gap closure in vector-expressing MSK-Leuk1 cells was obtained. The medium was replaced with fresh medium containing 25 mM HEPES buffer, and cells were allowed to incubate for 1 h at 37° C. A preset location was photographed every 10 min for a period of 16 h using the same microscope and camera set-up as above. The percentage of proliferating cells (those rounded up for cell division) was counted in this representative area.

Apoptosis assay. Apoptosis was assessed using the Guava Nexin kit (Millipore, Billerica, Mass.). Fifty thousand cells were plated per well in 6-well plates. After the appropriate treatment, floating cells were collected, combined with attached cells following trypsinization, and resuspended in DermaLife® K Medium (Lifeline Cell Technology, Walkersville, Md.) supplemented with 5% FBS. The cell suspension (100 µl) was incubated with 100 µl of Guava® Nexin Reagent for 20 min, according to the manufacturer's instructions. Two thousand cells were analyzed from each sample using the Guava® EasyCyte™ system, and the resulting data were expressed as a percentage of apoptotic cells (annexin V positive cells/total number of cells counted).

Cell proliferation. Fifty thousand cells/well were plated in 6-well plates. After the appropriate treatment, the DNA content of the cells, an indirect measure of proliferation, was determined using a Fluorescent DNA Quantitation kit (Bio-Rad Laboratories, Hercules, Calif.). In brief, cells were harvested, sonicated in 0.1×TEN assay buffer (Bio-Rad Laboratories) for 5 s, and incubated with a Hoechst dye mixture (BioRad Laboratories) for 1 h. Total DNA was measured using Fluoroscan Ascent FL (Thermo Fisher Scientific, Waltham, Mass.) at an excitation wavelength of 360 nm and an emission wavelength of 460 nm.

Results.

CYP1B1 deficiency decreases the motility of MSK-Leuk1 cells. To investigate the contribution of CYP1B1 to cancer progression, MSK-Leuk1 cells deficient in CYP1B1 were constructed using a lentivirus system to express shRNA specific to CYP1B1 mRNA. Western blot analyses indicated that CYP1B1 levels were decreased in cells expressing CYP1B1 shRNA, relative to control cells that expressed the vector (FIG. 1A).

The motility of CYP1B1-deficient MSK-Leuk1 cells was compared to that of cells expressing control vector (treated with either vehicle or E2). The rate of motility of CYP1B1-deficient cells measured as the ability of the cells to repopulate a scratched area of a previously confluent monolayer, was 54-57% lower than that of control cells expressing the basic vector ($P<0.0001$; FIGS. 1, B and C). Motility was not affected by E2 treatment. Rates of proliferation and apoptosis were comparable in CYP1B1 shRNA- and vector-expressing cells during the time period when cell migration was analyzed (16 h; see FIGS. 1, D and E).

To confirm that the observed gap closure was due to the migration and not proliferation of the cells, the motility of vector-expressing MSK-Leuk1 cells was observed in real time over a 16-h period. The cells were motile, with approximately 20% dividing during the observation period. No difference in proliferative rate was observed among the cells infiltrating the gap, as compared to the cell monolayer outside of the gap (data not shown).

Figure 2B:
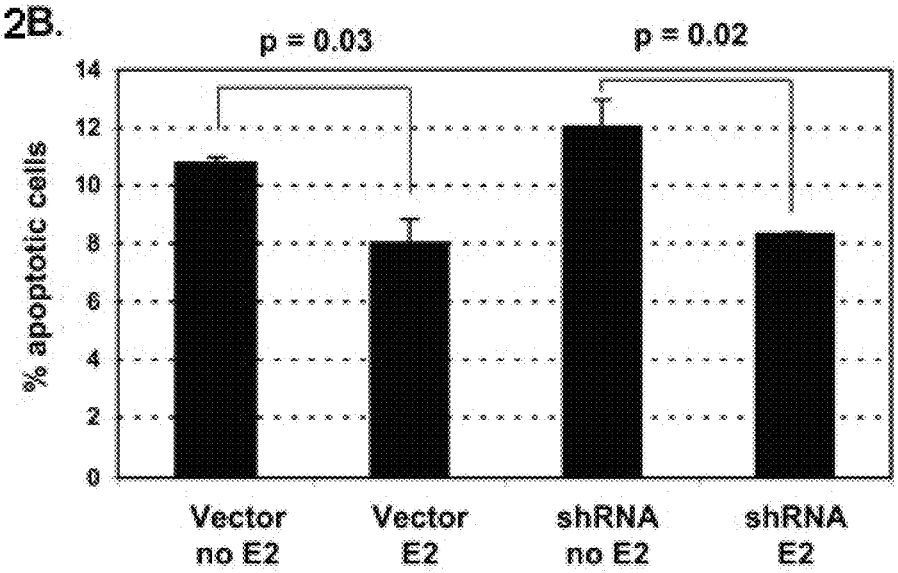
Figure 2C:
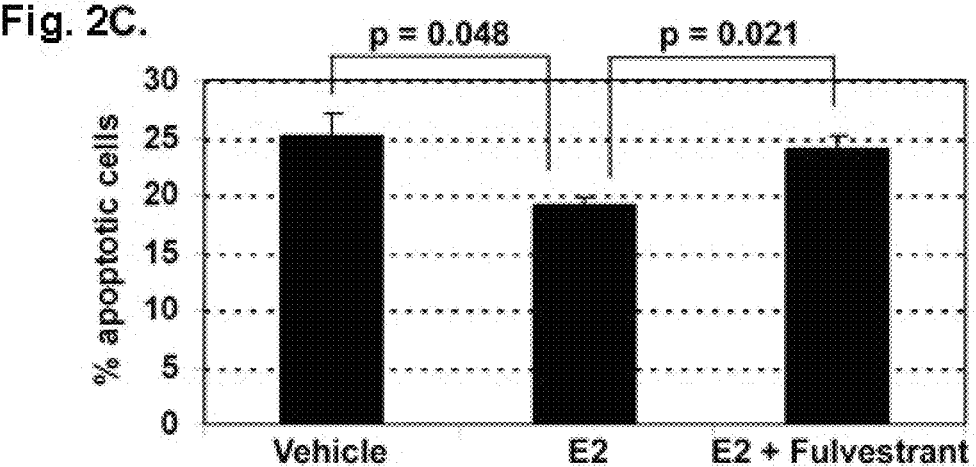

The effects of E2 exposure on the proliferation and apoptosis of cultured MSK-Leuk1 cells with or without CYP1B1 knockdown. To explore the role of E2 in head and neck carcinogenesis, MSK-Leuk1 cells expressing either vector or CYP1B1 shRNA were incubated in the presence or absence of E2 for 72 h. The proliferation of cells expressing CYP1B1 shRNA was decreased as compared to that of vector-expressing cells irrespective of E2 exposure (44.6% for vehicle-treated cells ($P=0.025$) and 47.6% for E2-treated cells ($P=0.006$), FIG. 2A). E2 exposure induced cell proliferation in vector-expressing cells by 10%; this increase, however, was not statistically significant (FIG. 2A). CYP1B1 depletion did not affect apoptosis (FIG. 2B). Exposure to E2, however, decreased apoptosis in both vector-expressing (by 25.5%, $P=0.030$) and CYP1B1 shRNA-expressing (by 30.1%, $P=0.015$) cells (FIG. 2B). This E2-mediated decrease in apoptosis was restored by the addition of the pure antiestrogen fulvestrant (FIG. 2C).

Example 2

Tobacco Smoke Modulation of Gene Expression in Lung Tissue

Materials and Methods.

Tobacco smoke exposure. Female A/J mice, 8 to 9 weeks of age, were purchased from The Jackson Laboratory and maintained with free access to food (AIN-93G, Harlan Teklad Global Diets) and water. Body weights were recorded weekly to monitor growth. All procedures were approved by the Institutional Animal Care and Use Committee of the University of Kentucky.

Mice were randomized into six treatment groups (six per group) and exposed to either tobacco smoke or HEPA-filtered ambient air (control). Exposure of mice to sidestream smoke was carried out in whole-body chambers for 6 hours per day, 5 days per week for 3, 8, and 20 weeks. Sidestream smoke was generated from the University of Kentucky reference cigarette (2R4F), and the suspended smoke particulate concentration in the chamber atmosphere was maintained at approximately 40 to 45 mg/m$^3$.

Exposure of mice to smoke was ascertained by measuring levels of urinary cotinine, ethoxyresorufin deethylase activity in lung microsomes, and cytochrome P450 1a1 (Cyp1a1) protein. Significant increases of these markers were observed in smoke-exposed groups over controls at all time points. Cotinine was measured routinely in urine samples (ELISA Kit, OraSure Technologies) collected from three to five mice per group over 24 hours. Cotinine values ranging from 4 to 10 µg cotinine/mg creatinine were observed in urine from smoke-exposed mice as compared with picogram levels in the unexposed control groups.

Lobes of lungs from three to four animals per treatment group were pooled, and lung microsomes were prepared by differential centrifugation (9,000×g and then 100,000×g for 60 minutes). The protein content of the resulting fraction was determined using a commercial kit from Bio-Rad. The ethoxyresorufin deethylase activity of lung microsomes was determined using a modified fluorimetric resorufin assay. Aliquots of the microsomal protein were separated on 12% SDS-polyacrylamide gels and subjected to Western blot analysis. Blots were probed with a polyclonal rabbit anti-rat Cyp1a1 antibody (diluted 1:800) from XenoTech LLC and secondary antirabbit antibody conjugated with alkaline phosphatase. Typical ethoxyresorufin deethylase activity levels (mean±SEM) were 1.21±0.3 and 9.74±1.4 pmol/min/mg protein for control and smoke-exposed groups, respectively. Immunoblots of lung microsomes probed with anti-Cyp1a1 antibody also showed significantly higher levels of protein in smoke-exposed mice.

At the time of sacrifice, lung tissue was excised from each animal, immediately placed in TRIzol (Invitrogen Corp.), and stored at −80° C. for subsequent RNA isolation and analysis. The remaining lung tissue was snap-frozen in liquid nitrogen for Cyp1a1 analyses.

RNA extraction and probe preparation. Frozen tissues were homogenized in TRIzol using a Polytron System PT 1200C (Kinematica AG), and total cellular RNA was extracted as recommended by the manufacturer. RNA concentration was determined by absorbance at 260 nm, and quality was assessed by monitoring the integrity of the 28S and 18S rRNAs by agarose gel electrophoresis.

Equal amounts of RNA from three animals were pooled, yielding two control and two smoke-exposed RNA pools per time point (3 and 8 weeks). To circumvent the potential contamination of normal lung tissue with neoplastic cells, samples collected at 20 weeks were evaluated individually, totaling six control and six smoke-exposed samples.

A total of 20 pooled (3 and 8 weeks) and individual (20 weeks) RNA samples (1 µg each) were subjected to one round of T7-based linear RNA amplification using the RiboAmp Kit (Molecular Devices). Universal mouse total RNA (Clontech Laboratories, Inc.) was also subjected to one round of amplification and served as a common reference for all hybridizations. cDNA probes were synthesized in duplicate by a standard reverse transcription reaction using 2 µg of each amplified RNA and labeled by indirect (amino-allyl) incorporation of Cy3 or Cy5 (CyDye Post-Labeling Reactive Dyes, Amersham Biosciences Corp.; dye-flip replicates). The concentration of the labeled cDNA probe was determined using an ND-1000 spectrophotometer (NanoDrop Technologies, Inc.).

cDNA microarray hybridization. The expression profile of samples was established using a mouse microarray containing 15,552 (15K) cDNA clones obtained from the Institute of Aging, NIH and printed in house. Probe hybridizations were performed following standard procedures. Following hybridization, the slides were scanned with a GMS 428 scanner (Affymetrix) at full laser intensity and variable photomultiplier tube voltage settings, capturing the full dynamic range for each slide in each respective channel. Image segmentation and spot quantification were done with the ImaGene software, version 5.6.1 (BioDiscovery), using the original default settings of the software. The mean intensities of signal and local background were extracted for each spot and subjected to analysis.

Mathematical analyses. Microarray data were processed and analyzed using R (http://www.r-project.org/) and the Bioconductor (Gentleman R C et al. (2004) Genomoe Biol 5:R80) platform. Only spots with GenBank accession entries (n=15,245) were considered for analysis. Background correction was carried out using the normexp method (Ritchie M E et al. (2007) 23:2700-7) implemented in the Bioconductor package limma (Linear Models for Microarray Data), with an offset of 50. This method has been found to be preferable to local background subtraction in most cases. LOWESS (locally weighted regression and smoothing scatter) normalization was used to correct for intensity-dependent dye bias. Dye-swap replicates were considered as replicates for statistical comparisons. To identify genes that were differentially expressed between smoke-exposed and reference samples, an empirical Bayes moderated t test, as implemented in limma (Smyth G K. (2004) Stat. Appl. Genet. Mol. Biol. 3: Article 3), was used. Due to differences in the sample design, the differential expression analysis was carried out separately for samples at 3 and 8 weeks (pooled samples) and 20 weeks (individual samples). Lists of differentially expressed genes for downstream analyses were selected using a P value threshold of 0.001.

Ingenuity Pathways Analysis (IPA version 6.3) was used to search for underlying biological pathways and molecular networks. IPA provides a rich functional annotation of genes and proteins and protein-protein interactions as well as the role of genes in various diseases. The genes differentially expressed at all time points (3, 8, and 20 weeks) were uploaded into IPA along with the corresponding fold change values. These genes are searched in the IPA functional annotation database called Ingenuity Pathways Knowledge Database (IPKB). Depending on the input gene list, the Ingenuity software models networks and pathways through a statistical computation using functional relationships such as interaction, activation, and localization between proteins, genes, complexes, cells, tissues, drugs, and diseases. Given a list of genes and their expression values or fold changes, IPA computes a score (P value) for network eligible genes. A higher score implies a significant composition of genes in a network.

Gas chromatography-coupled mass spectrometry. Female A/J mice (n=8) at 8 weeks of age were purchased from The Jackson Laboratory. At the time of sacrifice, the lung was perfused with 30 mL of saline and excised, and four lobes were stored at −80° C. for subsequent analysis by gas chromatography/mass spectrometry (GC/MS). Frozen lung tissues were homogenized in 30 mmol/L potassium phosphate buffer (pH 6.0) containing 0.5 mmol/L ascorbic acid. After adding methanol (60%, v/v), the homogenate was extracted twice with 1 volume of hexane. The aqueous phase was filtered using a 0.7-µm glass microfiber filter, extracted with 2 volumes of ethyl acetate, and evaporated to dryness. The samples were derivatized in acetonitrile using N,O-bis-(trimethylsilyl)trifluoroacetamide containing 1% trimethylchlorosilane. Deuterium-labeled E2 (d5-E2; C/D/N Isotopes, Inc.) was used as internal standard and was added before splitless injection into a HP6890 GC/MS instrument with capillary column (20 m×0.18 mm×0.18 µm, DB-5 ms, Agilent JW Scientific Columns, Agilent Technologies). Selective ion monitoring [m/z 342, 416, and 421 for estrone (E1), E2, and d5-E2, respectively] and retention times relative to d5-E2 were used to identify each compound.

Immunohistochemistry. Perfused lungs from three female A/1 mice were fixed in 10% formalin for 24 hours and subsequently embedded in paraffin for immunohistochemical analysis. Sections (4 µm) were dewaxed through incubation in xylene, followed by a graded alcohol series, ending in distilled water. Steam heat-induced epitope recovery was used before incubation with the primary antibody. Rabbit polyclonal antibodies for E2 (AR038-5R, Biogenex), ERβ (51-7700, Zymed Laboratories), and a mouse monoclonal antibody for ERα (clone ER88, Biogenex) were used. All sections were developed using standard immunohistochemical protocols.

Quantitative real-time PCR. Primers specific for each murine gene of interest were purchased from Applied Biosystems, Inc., as follows: Cyp1b1 (assay ID: Mm00487229_m1), Cry1 (assay ID: Mm00514392_m1), Cbr3 (carbonyl reductase 3; assay ID: Mm00557339_m1), Ces3 (carboxylesterase 3; assay ID: Mm00474816_m1), Col3a1 (collagen, type III, α1; assay ID: Mm00802331_m1), Hdc (histidine decarboxylase; assay ID: Mm00456104_m1), Tef (thyrotrophic embryonic factor; assay ID: Mm00457513_m1), Ugt1a6a (UDP-glycosyltransferase 1 family, polypeptide A6; assay ID: Mm01967851_s1), and Hprt1 (hypoxanthine guanine phosphoribosyl transferase; assay ID: Mm00446968_m1). Total RNA (1 µg) was converted to cDNA using the High Capacity cDNA Archive Kit (Applied Biosystems).

Quantitative real-time PCR reactions were done in quadruplicate in an Applied Biosystems 7900HT Fast Real-Time PCR System using universal conditions. Data for each test gene and the housekeeping gene (Hprt1) were obtained in the form of threshold cycle number (Ct) for each time point (3, 8, and 20 weeks) and treatment condition (control and smoke treated). The Ct values for each gene (at each time point) were normalized to the housekeeping gene, and ΔCt values for samples from smoke-treated and control groups were compared using the Mann-Whitney test. The step-up method of Benjamini and Hochberg (Benjamini Y et al. (1995) J. Royal Stat. Soc. Series B; 57:289-300) was used to account for multiple hypotheses testing, and the false discovery rate (FDR) was computed for each gene. An FDR cutoff of 0.10 was used to declare statistical significance. The fold change in the transcript levels of samples from smoke-treated and control groups was computed at each time point using the comparative Ct method (ΔΔCt; Applied Biosystems Reference Manual, User Bulletin #2).

Western blot analysis. Fifty micrograms of pulmonary microsomal protein isolated from human smokers and non-smokers (XenoTech LLC) were separated by 10% SDS-PAGE (Bio-Rad) and electroblotted onto a polyvinylidene fluoride membrane. Membranes were blocked for 1 hour at room temperature in TBS with Tween 20 [TBST; 50 mmol/L Tris-HCl (pH 7.5), 150 mmol/L NaCl, 0.1% Tween 20] containing 5% nonfat milk and incubated overnight at 4° C. with primary antibodies. Primary antibodies against CYP1B1 and HPRT were purchased from ImgenexCorp. and Abcam, Inc., respectively.

After washing three times with TBST, the membranes were incubated with horseradish peroxidase-conjugated goat anti-rabbit IgG secondary antibody (Bio-Rad) for 1 hour at room temperature, rinsed with TBST, and visualized using ECL Western Blotting Detection Reagents (GE Healthcare).

Results.

Genes modulated by tobacco smoke exposure. Using a 15K mouse cDNA array, the global gene expression profile of murine lung tissue from female A/J mice exposed to tobacco smoke was compared with that of age-matched control mice maintained in HEPA-filtered ambient air. After normalization, a strong correlation (r>0.8) was observed among all dye-swap replicates as well as between two pools of samples (n=3 mice per pool) from the same treatment group (data not shown).

Figure 3A:
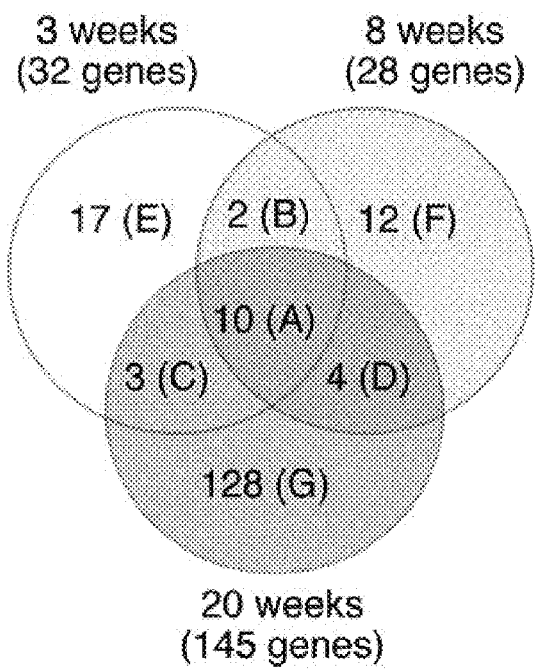
FIG. 3A and FIG. 3B show genes differentially expressed following 3, 8, and 20 weeks of smoke exposure.
Figure 3B:
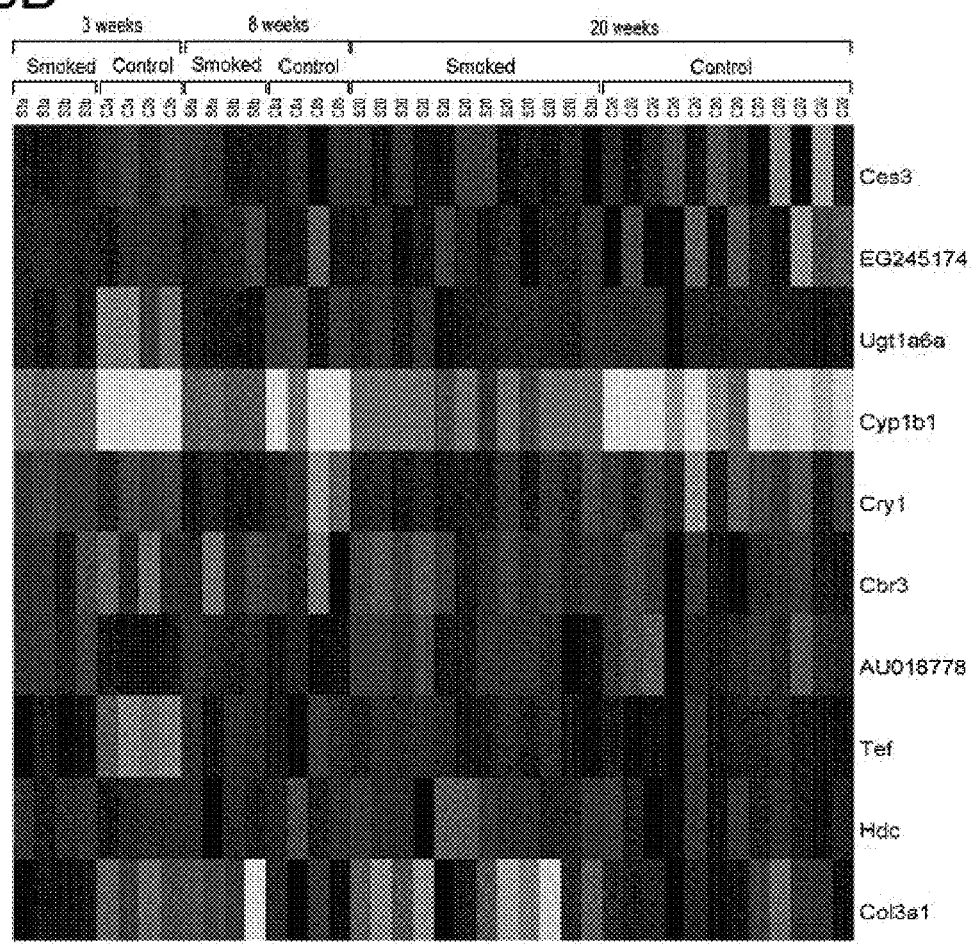

To identify early molecular changes induced by tobacco smoke, gene expression profiles from control and smoke-exposed lung tissues were determined following 3, 8, and 20 weeks of exposure. The expression of 32, 28, and 145 genes was modulated significantly by smoke following 3, 8, and 20 weeks, respectively (P=0.001; FIG. 3A). Ten genes were identified as differentially expressed at all time points (Group A, Table 1). The heat map represents fold change in the expression of these genes following 3, 8, and 20 weeks of exposure (FIG. 3B). Hierarchical clustering of the median corrected expression values of this subset of genes showed a precise separation of control and smoke-exposed samples (data not shown). Interestingly, the magnitude of the change in expression was similar for all smoke-exposed groups.

The single gene differentially expressed to the greatest extent (9- to 12-fold increase) in all smoke-exposed groups as compared with controls was Cyp1b1 (Table 1), a phase I detoxification enzyme involved in both the activation of carcinogens such as BaP and the metabolism of E2.

A surprising finding is the significant upregulation of cryptochrome 1 (Cry1), one of the key transcriptional regulators of circadian rhythm, in response to smoke exposure. After Cyp1b1, Cry1 was the gene differentially regulated to the greatest extent following 3 weeks of cigarette smoke exposure (fold change, 1.99; Table 1) and one of the 10 genes altered at all three time points after smoke exposure (FIG. 3).

TABLE 1

Genes differentially expressed following 3, 8, and 20 wk of smoke exposure

| Gene symbol | 3 wk | 8 wk | 20 wk |
|---|---|---|---|
| Group A | | | |
| Cyp1b1 | 11.38 | 8.19 | 9.81 |
| Cry1 | 2.66 | 2.04 | 2.18 |
| Cbr3 | 2.53 | 2.58 | 2.02 |
| Ugt1a6a | 2.52 | 1.67 | 1.73 |
| AU018778 | 1.88 | 1.63 | 2.02 |
| EG245174 | 1.85 | 1.90 | 1.58 |
| Ces3 | 1.80 | 1.74 | 1.64 |
| Tef | 1.79 | 1.79 | 1.38 |
| Hdc | 0.52 | 0.52 | 0.55 |
| Col3a1 | 0.42 | 0.41 | 0.49 |
| Group B | | | |
| Ier3 | 2.00 | 1.86 | — |
| Ttc21a | 0.54 | 0.50 | — |
| Group C | | | |
| Akr1c14 | 2.60 | — | 3.02 |
| Pdia6 | 0.64 | — | 0.60 |
| Igfbp3 | 0.47 | — | 0.54 |
| Group D | | | |
| Fkbp5 | — | 2.36 | 2.35 |
| Gsta4 | — | 2.02 | 1.81 |
| Hsp90aa1 | — | 0.58 | 0.68 |
| Ncald | — | 0.54 | 0.71 |

| Group E | | Group F | |
|---|---|---|---|
| Gene symbol | 3 wk | Symbol | 8 wk |
| Dnajb7 | 2.32 | Gc | 2.53 |
| Wipf3 | 1.98 | Serpina1e | 2.28 |
| Ppap2b | 1.84 | Tdrd5 | 1.78 |
| Gstm1 | 1.64 | Ephx1 | 1.76 |
| Lonrf3 | 1.64 | Tdrd7 | 1.57 |
| Tspan15 | 0.63 | Apol6 | 1.56 |
| Igf1 | 0.62 | Slco4c1 | 0.61 |
| Col1a2 | 0.60 | Dach1 | 0.53 |
| Cd34 | 0.58 | Mat2a | 0.52 |
| Arhgap28 | 0.58 | Axud1 | 0.52 |
| Plekha6 | 0.58 | Errfi1 | 0.50 |
| Fbp2 | 0.56 | Pitpnb | 0.38 |
| Npr3 | 0.53 | | |
| Igsf10 | 0.52 | | |
| D0H4S114 | 0.47 | | |
| Slc38a5 | 0.45 | | |
| Npnt | 0.40 | | |

| Group G | |
|---|---|
| Gene symbol | 20 wk |
| Scel | 2.06 |
| Igh-6 | 2.01 |
| Acsl1 | 1.90 |
| Adprhl2 | 1.85 |
| Nr1d2 | 1.83 |
| Mylpf | 1.81 |
| Cxcl1 | 1.80 |
| Gclc | 1.78 |
| Gpx2 | 1.72 |
| LOC100039206 | 1.66 |
| 4922501L14Rik | 1.61 |
| Slc40a1 | 1.58 |
| Fbln2 | 1.53 |
| Gmnn | 1.50 |
| Fabp3 | 1.48 |
| Bclaf1 | 1.48 |
| Tsix | 1.46 |
| Cldn12 | 1.45 |
| Tex12 | 1.44 |
| Cox7a2 | 1.42 |
| Slc39a4 | 1.41 |
| Bmp1 | 1.41 |
| Pigc | 1.41 |
| Ak3l1 | 1.41 |
| Gas1 | 1.40 |
| 1700020C11Rik | 1.40 |
| Elof1 | 1.40 |
| LOC100043812 | 1.39 |
| Ndufc1 | 1.39 |
| Gsto1 | 1.38 |
| Cabc1 | 1.38 |
| Prl3d1 | 1.38 |
| Hnrnpu | 1.37 |
| Fancm | 1.37 |
| Zfp11 | 1.37 |
| Apbb2 | 1.35 |
| Snx14 | 1.34 |
| Akr1c19 | 1.34 |
| Tmem57 | 1.33 |
| Esd | 1.32 |
| Josd3 | 1.32 |
| Sorbs1 | 1.31 |
| Appl2 | 1.31 |
| D19Ertd652e | 1.30 |
| Xdh | 1.30 |
| Vdac1 | 1.30 |
| Lias | 1.29 |
| RP23-292J1.1 | 1.27 |
| Bcnp1 | 1.27 |
| 1600020E01Rik | 1.27 |
| Tnk2 | 1.27 |
| Trhde | 1.26 |
| Gtf2a2 | 1.25 |
| Trub2 | 1.25 |
| Bach1 | 1.25 |
| Nfatc4 | 1.24 |
| Zfp612 | 1.24 |
| Krtap16-10 | 1.24 |
| Khdc1a | 1.23 |
| Ncdn | 1.22 |

TABLE 1-continued

Genes differentially expressed following
3, 8, and 20 wk of smoke exposure

| | |
|---|---|
| Ptp4a1 | 1.21 |
| Pygb | 0.84 |
| Cyhr1 | 0.84 |
| Ptpn6 | 0.83 |
| Maged2 | 0.83 |
| Col4a1 | 0.83 |
| Abca3 | 0.82 |
| Slc15a4 | 0.82 |
| Ankrd17 | 0.81 |
| Itgb7 | 0.81 |
| Ubr5 | 0.80 |
| Wdr79 | 0.79 |
| Srebf1 | 0.79 |
| Rhbdd3 | 0.79 |
| Stmn1 | 0.79 |
| Ubxd2 | 0.79 |
| Ptms | 0.79 |
| Pdia5 | 0.78 |
| Azin1 | 0.78 |
| Zdhhc18 | 0.78 |
| Gm2a | 0.76 |
| Bst2 | 0.75 |
| Rac2 | 0.75 |
| Selplg | 0.75 |
| Diablo | 0.74 |
| Dhrs3 | 0.74 |
| Tia1 | 0.73 |
| Mpv17 | 0.73 |
| Hba-a1 | 0.73 |
| Banp | 0.73 |
| Phtf1 | 0.73 |
| Gcap14 | 0.72 |
| Cybb | 0.72 |
| Stip1 | 0.72 |
| Laptm5 | 0.72 |
| Reps1 | 0.72 |
| Lmbr1 | 0.71 |
| Myo1e | 0.71 |
| Arf1 | 0.71 |
| Bbx | 0.71 |
| Cbx5 | 0.71 |
| Tbcld15 | 0.71 |
| Sdc4 | 0.70 |
| Comtd1 | 0.70 |
| Xbp1 | 0.70 |
| Lpcat1 | 0.70 |
| Igtp | 0.69 |
| Ywhaq | 0.69 |
| 9030425E11Rik | 0.68 |
| Rnf113a1 | 0.68 |
| Hsp90ab1 | 0.67 |
| Tcfcp2l1 | 0.67 |
| Ipo5 | 0.66 |
| Ahcyl2 | 0.65 |
| Ndst1 | 0.65 |
| LOC100043546 | 0.65 |
| Aspm | 0.64 |
| H2-K1 | 0.64 |
| Hbb-b1 | 0.64 |
| Thra | 0.63 |
| 2810025M15Rik | 0.63 |
| Leo1 | 0.62 |
| 5830443L24Rik | 0.60 |
| Rlbp1l1 | 0.60 |
| Lrp2 | 0.58 |
| Spnb2 | 0.57 |
| Sparc | 0.56 |
| Smc1b | 0.54 |

NOTE:
Differentially expressed genes were identified using the limma package with a P value threshold of 0.001. Categorization of genes (Groups A-G) corresponds to the same classification in FIG. 1A. Values represent the fold change in linear scale.

Quantitative real-time PCR and Western blot analysis. Differential expression of the genes that were modulated at all three time points and have a known function (7 of the 10 genes, Group A, Table 1) was validated by real-time PCR. All genes tested showed at least a 2-fold change in relative quantitation or had a FDR of <0.10, thereby validating the cDNA microarray results. The results for the 3-, 8-, and 20-week time points are presented in Table 2. A strong correlation was observed between the fold changes in gene expression determined by cDNA microarray and reverse transcription-PCR (Spearman's ρ was 0.9, 0.79, and 0.9 for samples obtained after 3, 8, and 20 weeks of smoke exposure, respectively).

TABLE 2

Gene expression analyses by quantitative real-time PCR

| | 3 wk | | | 8 wk | | | 20 wk | | |
|---|---|---|---|---|---|---|---|---|---|
| Gene | P | FDR | Fold change | P | FDR | Fold change | P | FDR | Fold change |
| Cyp1b1 | 2.16e−03 | 4.33e−03 | 22.58 | 2.16e−03 | 2.89e−03 | 22.58 | 2.16e−03 | 3.46e−03 | 19.05 |
| Cry1 | 2.16e−03 | 4.33e−03 | 4.30 | 2.16e−03 | 2.89e−03 | 2.79 | 2.16e−03 | 3.46e−03 | 2.94 |
| Cbr3 | 2.16e−03 | 4.33e−03 | 3.56 | 2.16e−03 | 2.89e−03 | 2.55 | 2.16e−03 | 3.46e−03 | 2.79 |
| Ces3 | 6.49e−02 | 6.49e−02 | 2.38 | 8.66e−03 | 9.89e−03 | 1.68 | 4.11e−02 | 4.70e−02 | 1.57 |
| Tef | 2.16e−03 | 4.33e−03 | 2.53 | 6.49e−02 | 6.49e−02 | 1.54 | 4.33e−03 | 5.77e−03 | 1.87 |
| Ugt1a6a | 6.49e−02 | 6.49e−02 | 1.71 | 2.16e−03 | 2.89e−03 | 2.58 | 6.49e−02 | 6.49e−02 | 1.46 |
| Col3a1 | 1.52e−02 | 2.42e−02 | 0.54 | 2.16e−03 | 2.89e−03 | 0.30 | 2.16e−03 | 3.46e−03 | 0.38 |
| Hdc | 6.49e−02 | 6.49e−02 | 0.91 | 2.16e−03 | 2.89e−03 | 0.43 | 2.16e−03 | 3.46e−03 | 0.43 |

NOTE:
Total RNA was assayed by reverse transcription-PCR. Samples were analyzed in quadruplicate, and the resulting data were expressed as the average cycle threshold ($C_t$). The housekeeping gene Hprt1 was used for data normalization ($\Delta C_t$). Comparisons between control and smoke-exposed samples for statistical significance were determined using the Mann-Whitney test (P value) and the step-up method of Benjamini and Hochberg (FDR). Fold change was calculated using the comparative $C_t$ method ($\Delta\Delta C_t$). Genes induced or repressed following smoke exposure are indicated by a fold change >1 or <1, respectively.

Figure 4:
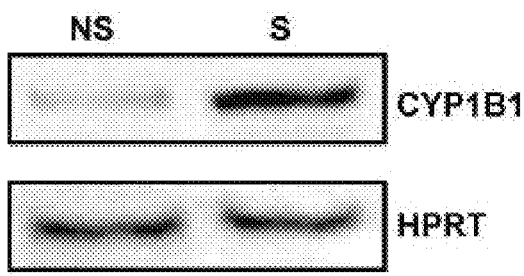
FIG. 4 shows a Western blot analysis of CYP1B1 in human pulmonary microsomes from nonsmokers (NS) and smokers (S). Each sample (50 µg) contains a pool of microsomal protein from four individuals of mixed genders. HPRT was used as a loading control.
Figure 5A:
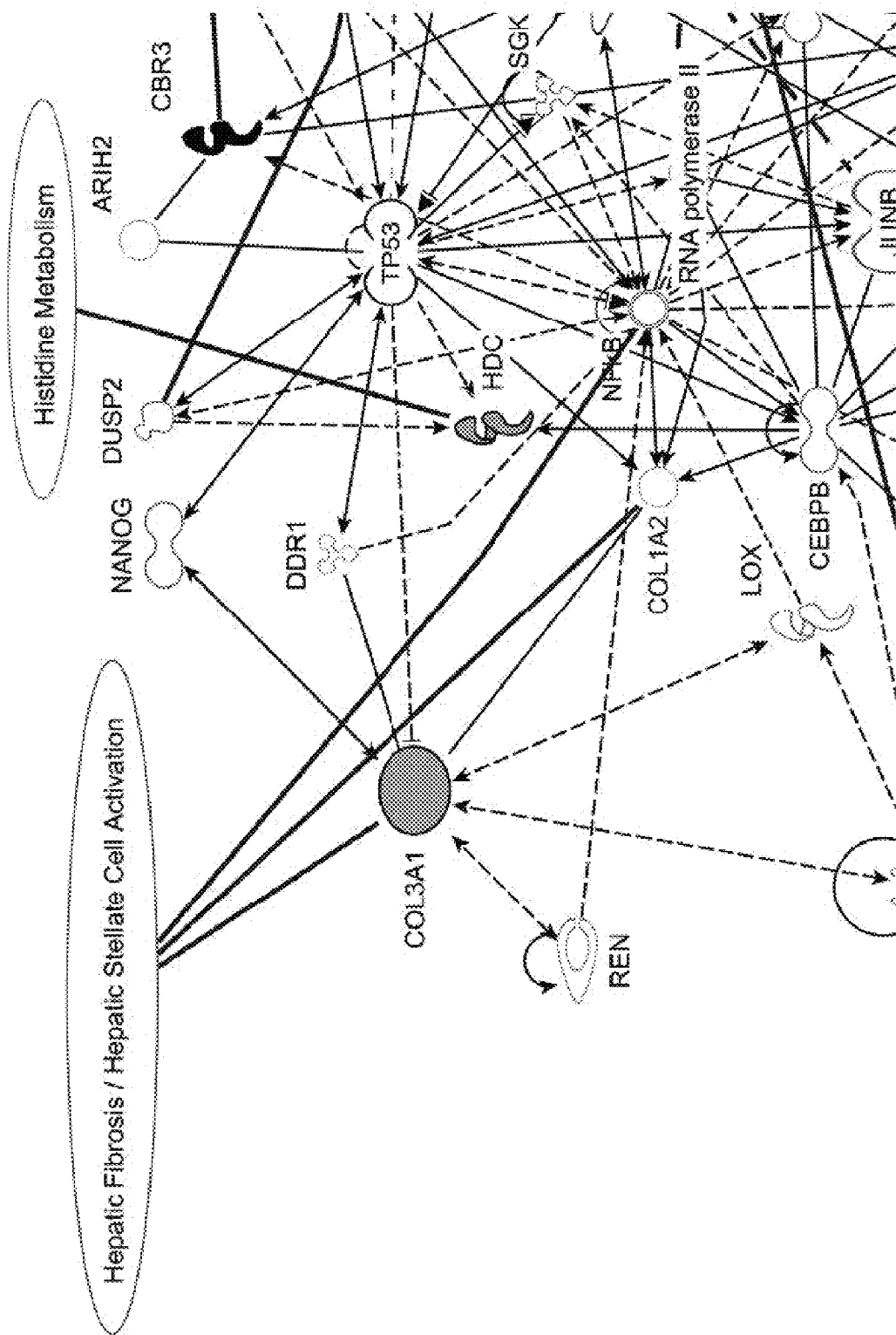
FIG. 5A-D shows a network of genes differentially expressed in common following 3, 8, and 20 wk of smoke exposure. Differentially expressed genes (n=7) are depicted as a network with overlaid functions and pathways according to Ingenuity Pathways Analysis Software. COL3A1 and HDC are downregulated, and CBR3, CYP1B1, CRY1, TEF, and UGT1A6 are upregulated. The remaining genes are involved in the network through direct or indirect interactions. Lines connecting Cyp1b1 to other genes indicate a direct relationship with Cyp1b1 (protein-protein interaction or protein-DNA). For example, the Ahr-Arnt complex increases transcription of Cyp1b1 in mammals. Lines with balloons indicate gene function or a pathway in which a gene is involved.
Figure 5B:
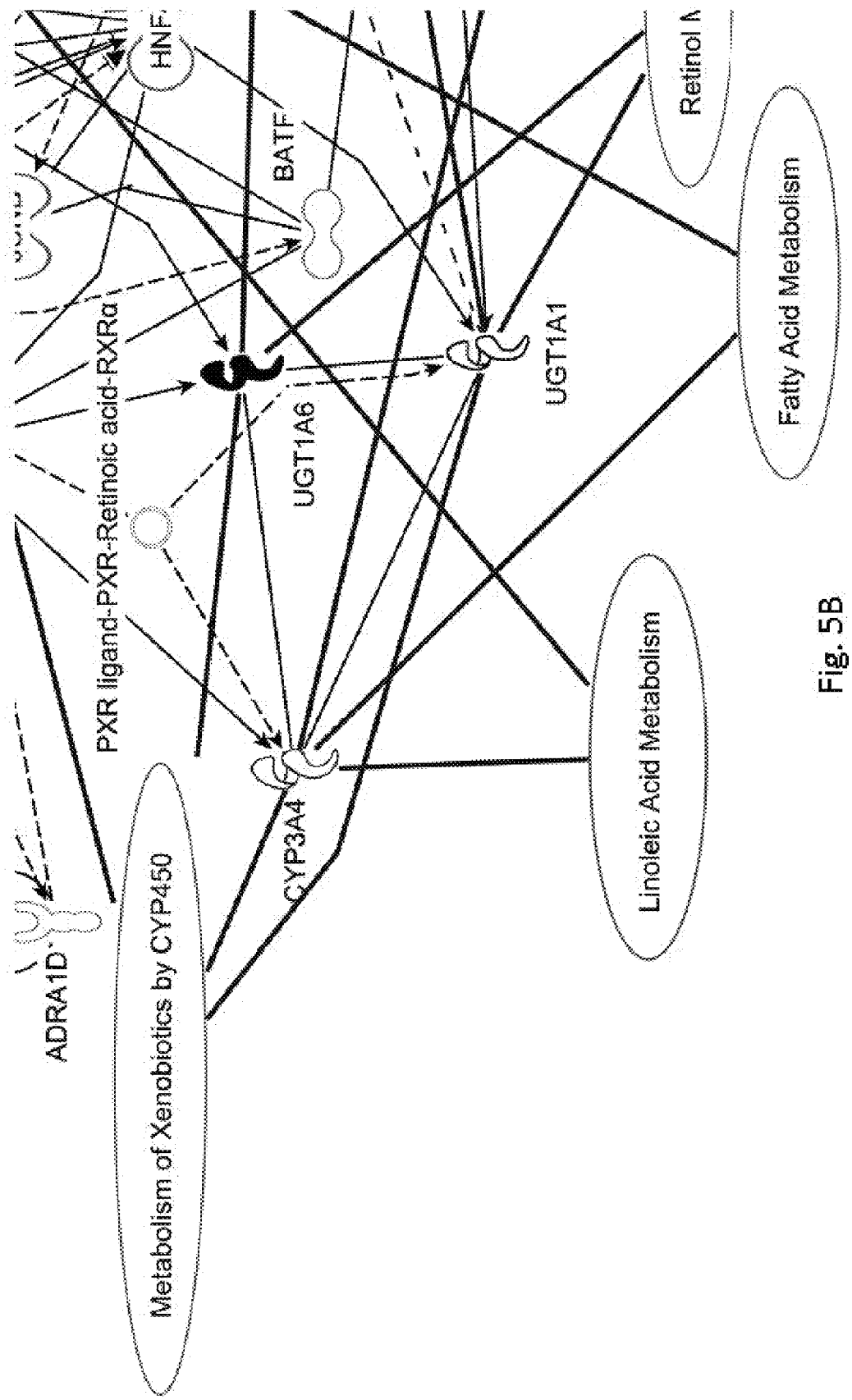
Figure 5C:
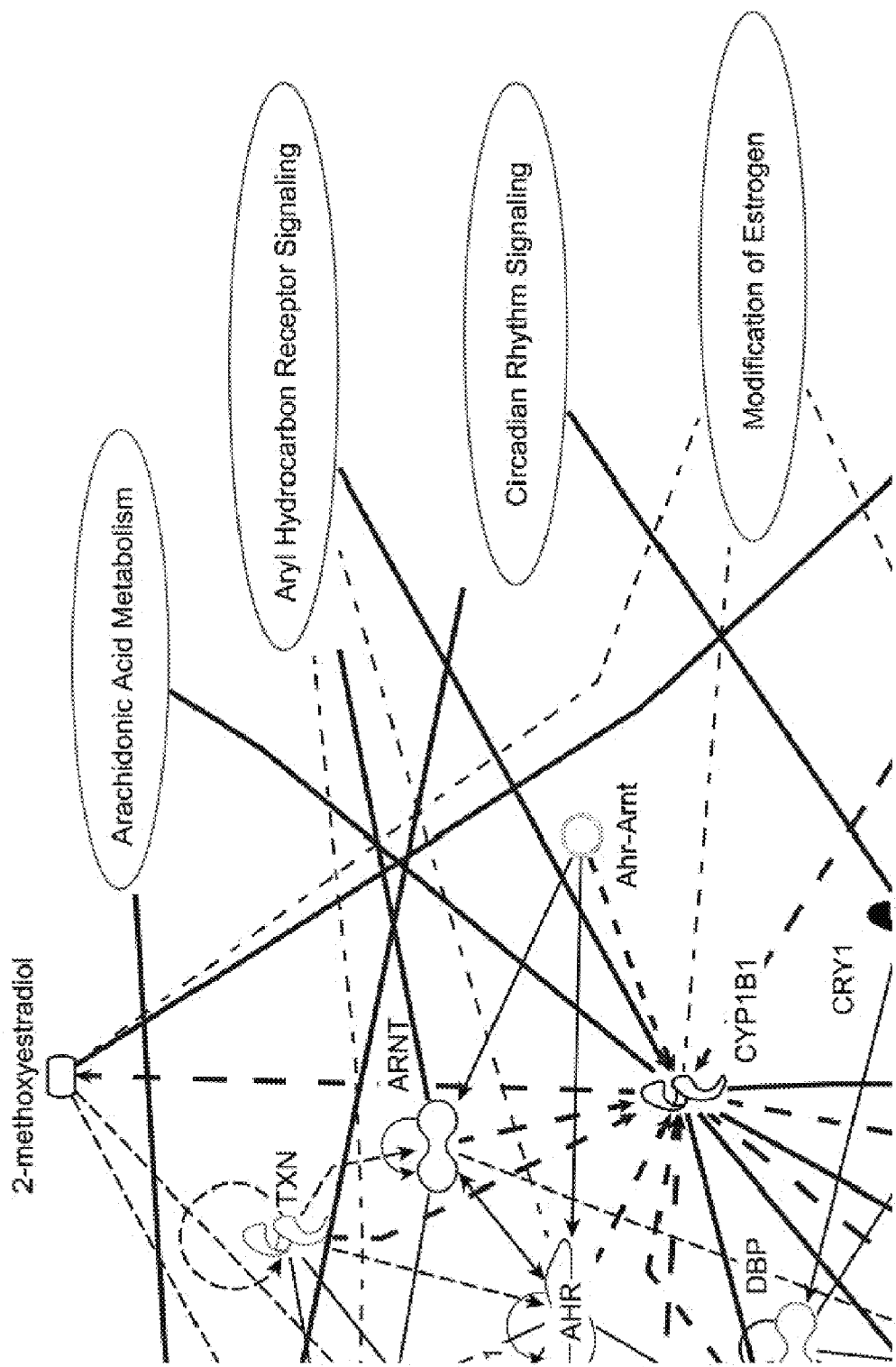
Figure 5D:
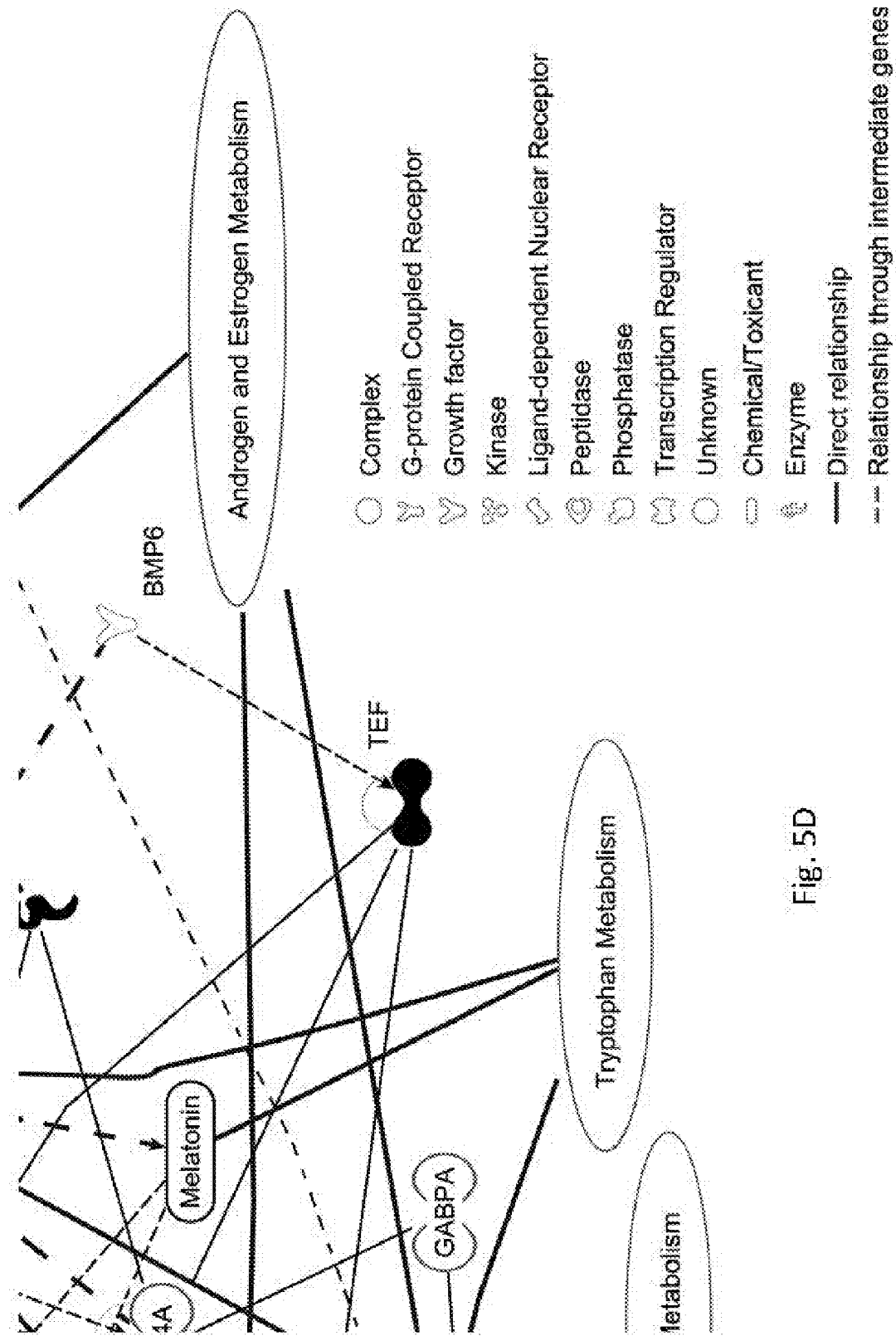

Examination of three commercial antibodies for their specificity for mouse CYP1B1 indicated that none were highly specific for the protein of interest when analyzed by Western blot. For this reason, the ability of smoke to increase CYP1B1 mRNA expression was validated at the protein level using pooled preparations of human lung microsomes. Western blot analyses revealed a significant elevation in CYP1B1 protein in microsomes from smokers as compared with non-smokers. These data not only confirm that both CYP1B1 mRNA and protein levels are elevated after smoke exposure but also indicate the relevance of the murine finding to humans (FIG. 4).

Identification of biological pathways and networks modulated by tobacco smoke. In addition to identifying individual genes differentially expressed (fold change), a complementary strategy was used to identify biological pathways and networks modulated by short-term exposure to tobacco smoke. The fold changes of the 10 genes differentially expressed at all time points (3, 8, and 20 weeks of smoke exposure) were mapped through a statistical computation method (Ingenuity Pathways Analysis Software). FIGS. 5A-D depicts a highscoring network based on 7 of 10 genes that were eligible for network construction. In addition, canonical pathways and significant functions were mapped onto this network.

Consistent with induction of Cyp1b1 and its role in estrogen metabolism, oxidation of estrogen was identified as part of the network significantly modulated by tobacco smoke exposure, as highlighted in FIGS. 5A-D. Cyp1b1 was also present in several other pathways identified as being altered by smoke exposure, including metabolism of xenobiotics by cytochrome P450, linoleic acid metabolism, fatty acid metabolism, and tryptophan metabolism.

Additional pathways modulated by smoke exposure are indicated in FIGS. 5A-D and include hepatic fibrosis, histidine metabolism, arachidonic acid metabolism, aryl hydrocarbon receptor signaling, and circadian rhythm signaling. Further studies are required to determine if either activation or repression of these biological pathways contributes to smoke-induced lung tumorigenesis.

Detection and localization of estrogens within murine lung tissue. Although metabolism of estrogen is an important activity of Cyp1b1, this hormone had not been detected in murine lung tissue previously. A sensitive GC/MS method was established for the detection of E2 and E1, which can be converted to E2. Solvent extraction and GC/MS protocols were developed using standard solutions of the compounds E1 and E2. Lung tissue extracts were mixed with known amounts of E1 and E2 before extraction to assess recovery. Representative chromatograms of standards and extracts of lung tissue, illustrating the ions monitored, are presented in FIG. 6.

Analysis of lung tissue from eight untreated female mice clearly showed the presence of both E1 and E2 in extracts. The limit of detection per injection for E1 and E2 standards was 0.03 pmol, and the recoveries were 93% and 91%, respectively. However, the recovery of each compound from tissue was lower (E1, 29%; E2, 28%). Therefore, the actual concentration of estrogens in lung tissue could not be quantified due to low recovery. Efforts are under way to optimize the recovery and expand the methods to measure a full panel of estrogen metabolites.

The cellular localization of E2 within female murine lung tissue was determined by immunohistochemistry. Estrogen receptors (ERα and ERβ) were also examined to determine if ER-mediated estrogen signaling could occur within lung tissue. Staining for all antigens was localized primarily to the bronchial and bronchioloalveolar epithelium. Strong nuclear and cytoplasmic staining of E2 was observed, whereas staining of ERα and ERβ was localized primarily to the cytoplasm and nucleus, respectively (FIG. 6). No positive staining was detected in sections incubated with nonimmune IgG (negative control; data not shown). Because this observation was purely qualitative, additional quantitative analyses of immunostained sections of untreated and smoke-exposed lung tissues are required to validate the observed subcellular localization of ER expression. Nevertheless, intracellular localization of E2 when combined with its detection by GC/MS in perfused lungs, as done in this study, ensures that estrogens are present within murine lung tissue (as opposed to only in the circulation).

Example 3

Selective Inhibition of CYP1B1

The goal of these experiments was to evaluate the effect of chemical inhibition of CYP1B1 on the motility of head and neck cells. Homoeriodictyol, a known naturally occurring flavonoid and a selective inhibitor of CYP1B1 (Doostdar H. et al., (2000) Toxicology 144:31-38) was used in this study.

Figure 7:
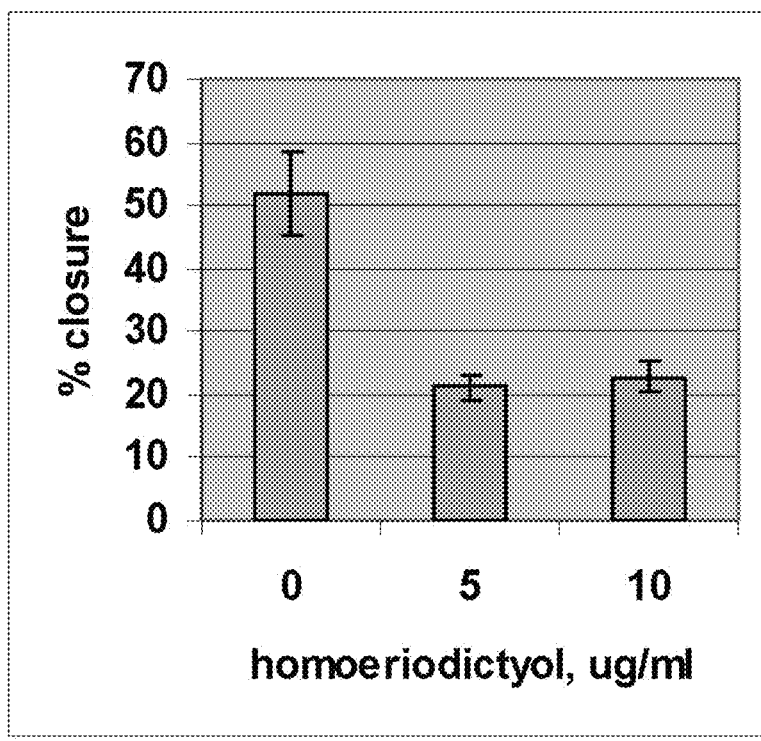
FIG. 7. shows that homoeriodictyol treatment inhibited motility of MSK-Leuk1 cells 2.3-2.5-fold compared to vehicle-only controls.

Cell motility assay. MSK-Leuk1 cells were incubated with either vehicle (ethanol, final concentration 0.01% in the medium) or homoeriodictyol at concentrations of 5 and 10 µg/ml for 5 days and the medium with either vehicle or homoeriodictyol was every other day. At the end of the fifth day, the cells were plated at 100% confluence in the medium containing either vehicle or homoeriodictyol. Twenty-four hours later the surface of the cell culture dish was carefully scratched using a micropipette tip, thus making an evenly distributed gap in the cell monolayer. The cells were washed with PBS and fresh medium (containing either vehicle or homoeriodictyol) was added. At least 10 representative images of each gap were acquired at 0 h and 17 h of incubation using a Nikon TE-2000U wide field inverted microscope (Optical Apparatus Co., Ardmore, Pa.) equipped with a Roper Scientific Cool Snap HQ camera. The area devoid of cells was measured on every image using MetaMorph 7.0 (Molecular Devices, Inc., Sunnyvale, Calif.). Gap closure was expressed as a percentage of total gap area at baseline and calculated as follows: (area at 0 h−area at 17 h)/(area at 0 h)*100%. Treatment of cells with homoeriodictyol at concentrations of 5 and 10 µg/ml inhibited cells motility by 2.5-2.3 fold, as compared to vehicle-treated control (FIG. 7).

Follow-up studies will assess apoptosis and cell proliferation. Apoptosis will be assessed using the Guava Nexin kit (Millipore, Billerica, Mass.). Cells will be incubated with a CYP1B1 inhibitor under conditions used for the motility experiment. Floating cells will be collected, combined with attached cells following trypsinization and resuspended in the medium. The cell suspension (100 µl) will be incubated with 100 µl of Guava Nexin Reagent for 20 min, according to the manufacturer's instructions. Two thousand cells will be analyzed from each sample using the Guava EasyCyte system, and the resulting data will be expressed as a percentage of apoptotic cells (annexin V positive cells/total number of cells counted).

To evaluate cell proliferation, cells will be incubated with a CYP1B1 inhibitor under conditions used for the motility experiment. The DNA content of the cells, an indirect measure of proliferation, will be determined using a Fluorescent DNA Quantitation kit (Bio-Rad Laboratories, Hercules, Calif.). Cells will be harvested, sonicated in 0.1×TEN assay buffer (Bio-Rad Laboratories) for 5 s, and incubated with a Hoechst dye mixture (BioRad Laboratories) for 1 h. Total DNA will be measured using Fluoroscan Ascent FL (Thermo Fisher Scientific, Waltham, Mass.) at an excitation wavelength of 360 nm and an emission wavelength of 460 nm.

The effect of CYP1B1 inhibition on apoptosis and proliferation of head and neck or lung cells will be further evaluated over a longer incubation period. Cells will be exposed to a select concentration of CYP1B1 inhibitor for 72 h. Apoptosis (Guava Nexin kit) and cell proliferation (total DNA content) will be measured as described above.

Example 4

Antibodies to CYP1B1 for the Inhibition of CYP1B1

This is a prophetic example. The proposed experiments will evaluate the effect of antibody inhibition of CYP1B1 on the motility, proliferation and apoptosis of head and neck cells and lung cells. The antibody used may be any antibody known in the art that specifically binds to CYP1B1, or may be a new antibody produced by immunizing an animal with the CYP1B1 protein or a fragment thereof.

The antibodies may comprise any of the IgA, IgD, IgE, IgG, IgM, or IgY isotypes. The antibodies may be polyclonal, and preferably are monoclonal.

The antibodies may comprise post-translational modifications or moieties, which may impact antibody activity or stability. These modifications or moieties include, but are not limited to, methylated, acetylated, glycosylated, sulfated, phosphorylated, carboxylated, and amidated moieties and other moieties that are well known in the art. The antibodies may comprise derivatives or fragments or portions of antibodies that retain the antigen-binding specificity, for example, bispecific antibodies, diabodies, single-chain molecules, as well as Fab, F(ab')2, Fd, Fabc, and Fv molecules, single chain (Sc) antibodies, single chain Fv antibodies (scFv), individual antibody light chains, individual antibody heavy chains, fusions between antibody chains and other molecules, heavy chain monomers or dimers, light chain monomers or dimers, and dimers consisting of one heavy and one light chain. The antibodies may be chimeric antibodies. The antibodies may be humanized antibodies. The antibodies may be fully human antibodies.

Initial experiments will determine the minimal dose of the anti-CYP1B1 antibody that yields maximal inhibition of CYP1B1 biologic activity. Cells will then be treated with the antibody, and cell motility, proliferation, and apoptosis will be assessed as described above.

The invention is not limited to the embodiments described and exemplified above, but is capable of variation and modification within the scope of the appended claims.

We claim:

1. A method for reducing the risk of motility of premalignant cells of the lung, comprising
    a. isolating cells of the lung from a human subject;
    b. determining whether the cells are premalignant;
    c. if the isolated cells are premalignant, determining whether the level of mRNA encoding the cytochrome P450 1B1 (CYP1B1) protein or whether the level of the CYP1B1 protein is elevated in the isolated cells;
    d. if the level of mRNA encoding the CYP1B1 protein is elevated in the isolated cells, or if the level of CYP1B1 protein is elevated in the isolated cells, administering to the subject a flavonoid selected from the group consisting of hesperidin, hesperetin, diosmetin, diosmin, eriodictyol, and homoeriodictyol in an amount effective to inhibit the motility-promoting activity of CYP1B1 protein in premalignant cells of the lung in the subject, thereby reducing the risk that the premalignant cells will become motile.

2. The method of claim 1, wherein the subject has smoked tobacco.

3. The method of claim 1, wherein the flavonoid is homoeriodictyol.

4. The method of claim 1, wherein the premalignant cells of the lung are capable of transforming into a non-small cell lung cancer cell, a small cell lung cancer cell, a squamous cell carcinoma of the lung, an adenocarcinoma cell, an adenoma cell, or a bronchioalveolar carcinoma cell.

5. The method of claim 1, wherein the cells are determined to be premalignant, and wherein step (c) further comprises determining whether the level of mRNA encoding the collagen type III, alpha 1 (COL3A1) and histidine decarboxylase (HDC) proteins is reduced in the isolated cells, and determining whether the level of mRNA encoding the carbonyl reductase 3 (CBR3), cryptochrome 1 (CRY1), thyrotrophic embryonic factor (TEF), and UDP-glucuronosyltransferase 1A6 (UGT1A6) genes is elevated in the isolated cells, and step (d) comprises administering to the subject a flavonoid selected from the group consisting of hesperidin, hesperetin, diosmetin, diosmin, eriodictyol, and homoeriodictyol in an amount effective to inhibit the motility-promoting activity of CYP1B1 protein in premalignant cells of the lung in the subject if it is determined that the level of mRNA encoding the COL3A1 and HDC proteins is reduced in the isolated cells, and that the level of mRNA encoding the CBR3, CRY1, TEF, UGT1A6, and CYP1B1 proteins is elevated in the isolated cells.

6. The method of claim 1, wherein the cells are determined to be premalignant, step (c) comprises determining whether the level of mRNA encoding the CYP1B1 protein is elevated in the isolated cells, and step (d) comprises administering to the subject a flavonoid selected from the group consisting of hesperidin, hesperetin, diosmetin, diosmin, eriodictyol, and homoeriodictyol in an amount effective to inhibit the motility-promoting activity of CYP1B1 protein in premalignant cells of the lung in the subject if it is determined that the level of mRNA encoding the CYP1B1 protein is elevated in the isolated cells.

7. The method of claim 1, wherein the cells are determined to be premalignant, step (c) comprises determining whether the level of CYP1B1 protein is elevated in the isolated cells, and step (d) comprises administering to the subject a flavonoid selected from the group consisting of hesperidin, hesperetin, diosmetin, diosmin, eriodictyol, and homoeriodictyol in an amount effective to inhibit the motility-promoting activity of CYP1B1 protein in premalignant cells of the lung in the subject if it is determined that the level of CYP1B1 protein is elevated in the isolated cells.

8. A method for reducing the risk of motility of premalignant cells of the head and neck, comprising
    a. isolating cells of the head and neck from a human subject;
    b. determining whether the cells are premalignant;
    c. if the isolated cells are premalignant, determining whether the level of mRNA encoding the cytochrome P450 1B1 (CYP1B1) protein or whether the level of the CYP1B1 protein is elevated in the isolated cells;
    d. if the level of mRNA encoding the CYP1B1 protein is elevated in the isolated cells, or if the level of CYP1B1 protein is elevated in the isolated cells, administering to the subject a flavonoid selected from the group consisting of hesperidin, hesperetin, diosmetin, diosmin, eriodictyol, and homoeriodictyol in an amount effective to inhibit the motility-promoting activity of CYP1B1 protein in premalignant cells of the head and neck in the subject, thereby reducing the risk that the premalignant cells will become motile.

9. The method of claim 8, wherein the subject has smoked tobacco.

10. The method of claim 8, wherein the flavonoid is homoeriodictyol.

11. The method of claim 8, wherein the cells are determined to be premalignant, step (c) comprises determining whether the level of mRNA encoding the CYP1B1 protein is elevated in the isolated cells, and step (d) comprises administering to the subject a flavonoid selected from the group consisting of hesperidin, hesperetin, diosmetin, diosmin, eriodictyol, and homoeriodictyol in an amount effective to inhibit the motility-promoting activity of CYP1B1 protein in premalignant cells of the head and neck in the subject if it is determined that the level of mRNA encoding the CYP1B1 protein is elevated in the isolated cells.

12. The method of claim 8, wherein the cells are determined to be premalignant, step (c) comprises determining whether the level of CYP1B1 protein is elevated in the isolated cells, and step (d) comprises administering to the subject a flavonoid selected from the group consisting of hesperidin, hesperetin, diosmetin, diosmin, eriodictyol, and homoeriodictyol in an amount effective to inhibit the motility-promoting activity of CYP1B1 protein in premalignant cells of the head and neck in the subject if it is determined that the level of CYP1B1 protein is elevated in the isolated cells.

13. A method for reducing the risk of proliferation of premalignant cells of the head and neck, comprising
   a. isolating cells of the head and neck from a human subject;
   b. determining whether the cells are premalignant;
   c. if the isolated cells are premalignant, determining whether the level of mRNA encoding the cytochrome P450 1B1 (CYP1B1) protein or whether the level of the CYP1B1 protein is elevated in the isolated cells;
   d. if the level of mRNA encoding the CYP1B1 protein is elevated in the isolated cells, or if the level of CYP1B1 protein is elevated in the isolated cells, administering to the subject a flavonoid selected from the group consisting of hesperidin, hesperetin, diosmetin, diosmin, eriodictyol, and homoeriodictyol in an amount effective to inhibit the proliferation-promoting activity of CYP1B1 protein in premalignant cells of the head and neck in the subject, thereby reducing the risk that the premalignant cells will become motile.

14. The method of claim 13, wherein the subject has smoked tobacco.

15. The method of claim 13, wherein the flavonoid is homoeriodictyol.

16. The method of claim 13, wherein the cells are determined to be premalignant, step (c) comprises determining whether the level of mRNA encoding the CYP1B1 protein is elevated in the isolated cells, and step (d) comprises administering to the subject a flavonoid selected from the group consisting of hesperidin, hesperetin, diosmetin, diosmin, eriodictyol, and homoeriodictyol in an amount effective to inhibit the proliferation-promoting activity of CYP1B1 protein in premalignant cells of the head and neck in the subject if it is determined that the level of mRNA encoding the CYP1B1 protein is elevated in the isolated cells.

17. The method of claim 13, wherein the cells are determined to be premalignant, step (c) comprises determining whether the level of CYP1B1 protein is elevated in the isolated cells, and step (d) comprises administering to the subject a flavonoid selected from the group consisting of hesperidin, hesperetin, diosmetin, diosmin, eriodictyol, and homoeriodictyol in an amount effective to inhibit the proliferation-promoting activity of CYP1B1 protein in premalignant cells of the head and neck in the subject if it is determined that the level of CYP1B1 protein is elevated in the isolated cells.

* * * * *